US008420099B2

(12) United States Patent
Berger et al.

(10) Patent No.: US 8,420,099 B2
(45) Date of Patent: *Apr. 16, 2013

(54) CHIMERIC PROTEIN FOR PREVENTION AND TREATMENT OF HIV INFECTION

(75) Inventors: Edward A. Berger, Rockville, MD (US); Christie M. Del Castillo, San Francisco, CA (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 1075 days.

This patent is subject to a terminal disclaimer.

(21) Appl. No.: 11/535,957

(22) Filed: Sep. 27, 2006

(65) Prior Publication Data

US 2007/0243208 A1 Oct. 18, 2007

Related U.S. Application Data

(63) Continuation of application No. 09/936,702, filed as application No. PCT/US00/06946 on Mar. 16, 2000, now Pat. No. 7,115, 262.

(60) Provisional application No. 60/124,681, filed on Mar. 16, 1999.

(51) Int. Cl.
| A61K 39/21 | (2006.01) |
| C07H 21/02 | (2006.01) |
| C07H 21/04 | (2006.01) |
| C07K 14/00 | (2006.01) |
| C07K 16/08 | (2006.01) |
| C07K 16/42 | (2006.01) |

(52) U.S. Cl.
USPC ........ 424/192.1; 435/238; 435/325; 435/419; 435/69.7; 530/350; 530/387.2; 530/387.3; 530/395

(58) Field of Classification Search .................. None
See application file for complete search history.

(56) References Cited

U.S. PATENT DOCUMENTS

| 5,013,548 A | 5/1991 | Haynes et al. |
| 5,298,419 A | 3/1994 | Masuho et al. |
| 5,587,455 A | 12/1996 | Berger et al. |
| 5,591,828 A | 1/1997 | Bosslet et al. |
| 5,614,612 A | 3/1997 | Haigwood et al. |
| 5,637,481 A | 6/1997 | Ledbetter et al. |
| 5,643,756 A | 7/1997 | Kayman et al. |
| 5,695,927 A | 12/1997 | Masuho et al. |
| 5,756,674 A | 5/1998 | Katinger et al. |
| 5,767,260 A | 6/1998 | Whitlow et al. |
| 5,817,767 A | 10/1998 | Allaway et al. |
| 5,843,454 A | 12/1998 | Devico et al. |
| 5,843,882 A | 12/1998 | Boyd et al. |
| 5,856,456 A | 1/1999 | Whitlow et al. |
| 5,922,325 A | 7/1999 | Tilley et al. |
| 5,925,741 A | 7/1999 | Gershoni |
| 6,020,468 A | 2/2000 | Gershoni |
| 6,107,019 A | 8/2000 | Allaway et al. |
| 6,143,876 A | 11/2000 | Gershoni |
| 6,329,202 B1 | 12/2001 | Gershoni |
| 6,410,318 B1 | 6/2002 | Gershoni |
| 2003/0039663 A1 | 2/2003 | Devico et al. |

FOREIGN PATENT DOCUMENTS

| EP | 0 739 904 | 10/1996 |
| WO | WO 97/47318 | 12/1997 |
| WO | WO 98/36087 | 8/1998 |
| WO | WO 99/64073 | 12/1999 |

OTHER PUBLICATIONS

Greenspan et al. (Nature Biotechnology 7: 936-937, 1999).*
Alkhatib et al., "CC CKR5: A Rantes, MIP-1α, MIP-1β Receptor as a Fusion Cofactor for Macrophage-Tropic HIV-1," *Science* 272:1955-1958, Jun. 28, 1996.
Allaway et al., "Synergistic Inhibition of HIV-1 Envelope-Mediated Cell Fusion by CD4-Based Molecules in Combination with Antibodies to gp120 or gp41," *AIDS Research and Human Retroviruses* 9:581-587, 1993.
Balter, "Revealing HIV's T Cell Passkey," *Science* 280:1833-1834, Jun. 19, 1998.
Bandres et al., "Human Immunodeficiency Virus (HIV) Envelope Binds to CXCR4 Independently of CD4, and Binding Can Be Enhanced by Interaction with Soluble CD4 or by HIV Envelope Deglycosylation," *J Virol.* 72:2500-2504, Mar. 1998.
Boots et al., "Anti-Human Immunodeficiency Virus Type 1 Human Monoclonal Antibodies that Bind Discontinuous Epitopes in the Viral Glycoproteins Can Identify Mimotopes from Recombinant Phage Peptide Display Libraries," *Aids Research and Human Retroviruses* 13:1549-1559, 1997.
Bork P., "Powers and pitfalls in sequence analysis: the 70% hurdle," *Genome Research*, 10(4):398-400, 2000.
Bowie et al., "Deciphering the message in protein sequences: tolerance to amino acid substitutions," *Science*, 247(4948):1306-1310, 1990.
Broder and Berger, "Fusogenic selectivity of the envelope glycoprotein is a major determinant of human immunodeficiency virus type 1 tropism for CD4+ T-cell lines vs. primary macrophages," *Proc. Natl. Acad. Sci. USA* 92:9004-9008, Aug. 1995.
Broder et al., "The Block to HIV-1 Envelope Glycoprotein-Mediated Membrane Fusion in Animal Cells Expressing Human CD4 Can Be Overcome by a Human Cell Component(s)," *Virology* 13:483-491, 1993.
Broder and Berger, "CD4 Molecules with a Diversity of Mutations Encompassing the CDR3 Region Efficiently Support Human Immunodeficiency Virus Type 1 Envelope Glycoprotein-Mediated Cell Fusion," *J. Virol.* 67:913-926, Feb. 1993.

(Continued)

*Primary Examiner* — Robert A Zeman
(74) *Attorney, Agent, or Firm* — Klarquist Sparkman, LLP

(57) ABSTRACT

This invention relates to bispecific fusion proteins effective in viral neutralization. More specifically, such proteins have two different binding domains, an inducing-binding domain and an induced-binding domain, functionally linked by a peptide linker. Such proteins, nucleic acid molecules encoding them, and their production and use in preventing or treating viral infections are provided. One prototypical bispecific fusion protein is sCD4-SCFv(17b), in which a soluble CD4 fragment (containing domains D1 and D2) is fused to a single chain Fv portion of antibody 17b via a linker.

12 Claims, 4 Drawing Sheets

OTHER PUBLICATIONS

Byrn et al., "Biological properties of a CD4 immunoadhesin," *Nature* 344:667-670, Apr. 12, 1990.

Cao and Suresh, "Bispecific Antibodies as Novel Bioconjugates," *Bioconjugate Chem.* 9:635-645, 1998.

Capon et al., "Designing CD4 immunoadhesins for AIDS therapy," *Nature* 337:525-531, Feb. 9, 1989.

Cheong et al., "Affinity enhancement of bispecific antibody against two different epitopes in the same antigen," *Biochem. Biophys. Res. Comm.* 173:795-800, Dec. 31, 1990.

Cook and Wood, "Chemical synthesis of bispecific monoclonal antibodies: potential advantages in immunoassay systems," *J. Immunol. Meth.* 171:227-237, 1994.

D'Souza et al., "Evaluation of Monoclonal Antibodies to Human Immunodeficiency Virus Type 1 Primary Isolates by Neutralization Assays: Performance Criteria for Selecting Candidate Antibodies for Clinical Trials," *J. Infect. Dis.* 175:1056-1062, 1997.

Dey et al., "Neutralization of human immunodeficiency virus type 1 by sCD4-17b, a single-chain chimeric protein, based on sequential interaction of gp120 with CD4 and coreceptor," *J. Virol.* 77(5):2859-2865, 2003.

Feng et al., "HIV-1 Entry Cofactor: Functional cDNA Cloning of a Seven-Transmembrane, G Protein-Coupled Receptor," *Science* 272:872-877, May 10, 1996.

Fu et al., "Isolation and characterization of a monoclonal antibody that inhibits HIV-1 infection," *Microbes and Infection* 1:677-684, 1999.

Hanke and McMichael, "Design and construction of an experimental HIV-1 vaccine for a year-2000 clinical trial in Kenya," *Nature Med.* 6(9):951-955, Sep. 2000.

Ho et al., "Conformational Epitope on gp120 Important in CD4 Binding and Human Immunodeficiency Virus Type 1 Neutralization Identified by a Human Monoclonal Antibody," *J. Virol.* 65:489-493, Jan. 1991.

Idziorek and Klatzmann, "Construction of CD4-Based Chimeric Molecules by Chemical Cross-Linking," *AIDS Research. And Human Retroviruses* 7:529-536, 1991.

Kang et al., "Identification of a New Neutralizing Epitope Conformationally Affected by the Attachment of CD4 to gp120," *J. Immunol.* 151:449-457, Jul. 1, 1993.

Kwong et al., "Structure of an HIV gp120 envelope glycoprotein in complex with the CD4 receptor and a neutralizing human antibody," *Nature* 393:648-659, Jun. 18, 1998.

Liao et al., "Immunogenicity of constrained monoclonal antibody A32-human immunodeficiency virus (HIV) Env gp120 complexes compared to that of recombinant HIV type 1 gp120 envelope glycoproteins," *J. Virol.* 78(10):5270-5278, 2004.

McMichael and Hanke, "Is an HIV vaccine possible? Novel vaccines that induce cellular immunity can protect macaques from infection with simian immunodeficiency virus (643-650)," *Nature Med.* 5(6):612-614, Jun. 1999.

Mondor et al., "Human Immunodeficiency Virus Type 1 Attachment to HeLa CD4 Cells is CD4 Independent and gp120 Dependent and Requires Cell Surface Heparans," *J. Virol.* 72:3623-3634, May 1998.

Neri et al., "High-affinity Antigen Binding by Chelating Recombinant Antibodies (CRAbs)," *J. Mol. Biol.* 246:367-373, 1995.

Nussbaum et al., "Fusogenic Mechanisms of Enveloped-Virus Glycoproteins Analyzed by a Novel Recombinant Vaccinia Virus-Based Assay Quantitating Cell Fusion-Dependent Reporter Gene Activation," *J. Virol.* 68:5411-5422, Sep. 1994

Ridgway et al., "'Knobs-into holes' engineering of antibody $C_H3$ domains for heavy chain heterodimerization," *Prot. Eng.* 9:617-621, 1996.

Rizzuto et al., "A Conserved HIV gp120 Glycoprotein Structure Involved in Chemokine Rector Binding," *Science* 280:19491953, Jun. 19, 1998.

Robert-Guroff et al., "HTLV-III-neutralizing antibodies in patients with AIDS and AIDS-related complex," *Nature* 316-72-74, Jul. 4, 1985.

Roehr, *American Foundation for AIDS Research*, 3(4):1-8, 2002 (www.amfar.org/td).

Root et al., "Protein Design of an HIV-1 Entry Inhibitor," *Science* 291:884-888, Feb. 2, 2001.

Salzwedel et al., "Sequential CD4-coreceptor interactions in human immunodeficiency virus type 1 Env function: soluble CD4 activates Env for coreceptor-dependent fusion and reveals blocking activities of antibodies against cryptic conserved epitopes on gp120," *J. Virol.* 74(1):326-333, 2000.

Satrentau and Moore, "Conformational Changes Induced in the Human Immunodeficiency Virus Envelope Glycoprotein by Soluble CD4 Binding," *J. Exp. Med* 174:407-415, Aug. 1991.

Sullivan et al., "CD4-Induced Conformational Changes in the Human Immunodeficiency Virus Type 1gp120 Glycoprotein: Consequences for Virus Entry and Neutralization," *J. Virol.* 72:4694-4703, Jun. 1998.

Thali et al., "Characteriza6tion of Conserved Human Immunodeficiency Virus Type 1 gp120 Neutralization Epitopes Exposed upon gp120-CD4 Binding," *J. Virol.* 67:3978-3988, Jul. 1993.

Traunecker et al., "Bispecific single chain molecules (Janusins) target cytotoxic lymphocytes on HIV infected cells," *EMBO J.* 10:3655-3659, Dec. 1991.

Traunecker et al., "Janusin: new molecular design for bispecific reagents," *Int. J. Cancer* Supplement 7:51-52, 1992.

Trkola et al., "CD4-dependent, antibody-sensitive interactions between HIV-1 and its co-receptor CCR-5," *Nature* 384:184-187, Nov. 14, 1996.

Vermeire and Schols, "Specific CD4 down-modulating compounds with potent anti-HIV activity," *J. Leukocyte Biol.* 74:667-675, 2003.

Vodicka et al., "Indicator Cell Lines for Detection of Primary Strains of Human and Simian Immunodeficiency Viruses," *Virology* 233:193-198, 1997.

Wu et al., "CD4-induced interaction of primary HIV-1 gp120 glycoproteins with the chemokine receptor CCR-5," *Nature* 384:179-183, Nov. 14, 1996.

Wyatt et al., "Involvement of the V1/V2 Variable Loop Structure in the Exposure of Human Immunodeficiency Virus Type 1 gp120 Epitopes Induced by Receptor Binding," *J Virol.* 69:5723-5733, Sep. 1995.

Wyatt et al., "The antigenic structure of the HIV gp 120 envelope glycoprotein," *Nature* 393:705-711, Jun. 18, 1998.

Wyatt and Sodroski, "The HIV-1 Envelope Glycoproteins: Fusogens, Antigens, and Immuogens," *Science* 280:1884-1888, Jun. 19, 1998.

Huston et al., "Protein engineering of antibody binding sites: Recovery of specific activity in an anti-digoxin single-chain Fv analogue produced in *Esherichia coli*," *Proc. Natl. Acad. Sci.*, 85:5879-5883 (1988).

* cited by examiner

SEQUENCE LISTING

<160> NUMBER OF SEQ ID NOS: 11

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: linker peptide

<400> SEQUENCE: 1

-continued

```
Gly Gly Gly Gly Ser
 1               5

<210> SEQ ID NO 2
<211> LENGTH: 35
<212> TYPE: PRT
<213> ORGANISM: Artificial Sequence
<220> FEATURE:
<223> OTHER INFORMATION: Description of Artificial Sequence: seven
      repeat polypeptide linker

<400> SEQUENCE: 2

Gly Gly Gly Gly Ser Gly Gly Gly Gly Ser Gly Gly Gly Gly Ser Gly
 1               5                  10                  15

Gly Gly Gly Ser Gly Gly Gly Gly Ser Gly Gly Gly Gly Ser Gly Gly
             20                  25                  30

Gly Gly Ser
         35

<210> SEQ ID NO 3
<211> LENGTH: 508
<212> TYPE: PRT
<213> ORGANISM: Artificial Sequence
<220> FEATURE:
<223> OTHER INFORMATION: Description of Artificial Sequence:
      CD4-scFv(17b)

<400> SEQUENCE: 3

Met Asn Arg Gly Val Pro Phe Arg His Leu Leu Leu Val Leu Gln Leu
 1               5                  10                  15

Ala Leu Leu Pro Ala Ala Thr Gln Gly Lys Lys Val Val Leu Gly Lys
             20                  25                  30

Lys Gly Asp Thr Val Glu Leu Thr Cys Thr Ala Ser Gln Lys Lys Ser
         35                  40                  45

Ile Gln Phe His Trp Lys Asn Ser Asn Gln Ile Lys Ile Leu Gly Asn
     50                  55                  60

Gln Gly Ser Phe Leu Thr Lys Gly Pro Ser Lys Leu Asn Asp Arg Ala
 65                  70                  75                  80

Asp Ser Arg Arg Ser Leu Trp Asp Gln Gly Asn Phe Pro Leu Ile Ile
                 85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
        195                 200                 205

Gly Gly Gly Gly Ser Gly Gly Gly Gly Ser Gly Gly Gly Gly Ser Gly
    210                 215                 220

Gly Gly Gly Ser Gly Gly Gly Gly Ser Gly Gly Gly Gly Ser Gly Gly
225                 230                 235                 240

Gly Gly Ser Gln Val Gln Leu Leu Glu Ser Gly Ala Glu Val Lys Lys
```

|     |     |     | 245 |     |     |     | 250 |     |     |     | 255 |
|-----|-----|-----|-----|-----|-----|-----|-----|-----|-----|-----|-----|

Pro Gly Ser Ser Val Lys Val Ser Cys Lys Ala Ser Gly Asp Thr Phe
    260                265                270

Ile Arg Tyr Ser Phe Thr Trp Val Arg Gln Ala Pro Gly Gln Gly Leu
        275                280            285

Glu Trp Met Gly Arg Ile Ile Thr Ile Leu Asp Val Ala His Tyr Ala
    290                295              300

Pro His Leu Gln Gly Arg Val Thr Ile Thr Ala Asp Lys Ser Thr Ser
305              310              315            320

Thr Val Tyr Leu Glu Leu Arg Asn Leu Arg Ser Asp Asp Thr Ala Val
        325                330            335

Tyr Phe Cys Ala Gly Val Tyr Glu Gly Glu Ala Asp Glu Gly Glu Tyr
    340                345              350

Asp Asn Asn Gly Phe Leu Lys His Trp Gly Gln Gly Thr Leu Val Thr
        355                360            365

Val Thr Ser Gly Gly Gly Gly Ser Gly Gly Gly Ser Gly Gly Gly Gly
    370                375              380

Gly Ser Glu Leu Glu Leu Thr Gln Ser Pro Ala Thr Leu Ser Val Ser
385              390              395            400

Pro Gly Glu Arg Ala Thr Leu Ser Cys Arg Ala Ser Glu Ser Val Ser
        405                410            415

Ser Asp Leu Ala Trp Tyr Gln Gln Lys Pro Gly Gln Ala Pro Arg Leu
    420                425              430

Leu Ile Tyr Gly Ala Ser Thr Arg Ala Thr Gly Val Pro Ala Arg Phe
        435                440            445

Ser Gly Ser Gly Ser Gly Ala Glu Phe Thr Leu Thr Ile Ser Ser Leu
    450                455              460

Gln Ser Glu Asp Phe Ala Val Tyr Tyr Cys Gln Gln Tyr Asn Asn Trp
465              470              475            480

Pro Pro Arg Tyr Thr Phe Gly Gln Gly Thr Arg Leu Glu Ile Lys Leu
        485                490            495

Val Pro Arg Gly Ser Gly His His His His His His
    500                505

<210> SEQ ID NO 4
<211> LENGTH: 1440
<212> TYPE: DNA
<213> ORGANISM: Artificial Sequence
<220> FEATURE:
<223> OTHER INFORMATION: Description of Artificial Sequence:
    CD4-scFv(17b)

<400> SEQUENCE: 4

```
atgaaccggg gagtcccttt taggcacttg cttctggtgc tgcaactggc gctcctccca      60
gcagccactc agggaaagaa agtggtgctg ggcaaaaaag gggatacagt ggaactgacc     120
tgtacagctt cccagaagaa gagcatacaa ttccactgga aaaactccaa ccagataaag     180
attctgggaa atcagggctc cttcttaact aaaggtccat ccaagctgaa tgatcgcgct     240
gactcaagaa gaagcctttg ggaccaagga aacttccccc tgatcatcaa gaatcttaag     300
atagaagact cagatactta catctgtgaa gtggaggacc agaaggagga ggtgcaattg     360
ctagtgttcg gattgactgc caactctgac acccacctgc ttcaggggca gagcctgacc     420
ctgaccttgg agagcccccc tggtagtagc ccctcagtgc aatgtaggag tccaagggggt    480 aaaaacatac aggggggggaa gaccctctcc gtgtctcagc tggagctcca ggatagtggc     540
acctggacat gcactgtctt gcagaaccag aagaaggtgg agttcaaaat agacatcgtg     600
```

```
gtgctagctt tccagaaggc ctccggaggt ggcggtagtg ggggaggcgg ttcaggcgga    660
ggtggatccg gtggcggagg gtcgggcggg ggtggaagcg ggggtggcgg ctccggaggc    720
ggaggttcac aggtgcagct gctcgagtct ggggctgagg tgaagaagcc tgggtcctcg    780
gtgaaggtct cctgcaaggc ctctggagac accttcatca gatatagttt tacctgggtg    840
cgacaggccc ctggacaagg ccttgagtgg atgggaagga tcatcactat ccttgatgta    900
gcacactacg caccgcacct ccagggcaga gtcacgatta ccgcggacaa gtccacgagc    960
acagtctacc tggagctgcg gaatctaaga tctgacgata cggccgtata tttctgtgcg   1020
ggagtgtacg agggagaggc ggacgagggg gaatatgata ataatgggtt tctgaaacat   1080
tggggccagg gaaccctggt cacggtcacc tcaggtggcg gtggctccgg aggtggtggg   1140
agcggtggcg gcggatctga actcgagttg acgcagtctc cagccaccct gtctgtgtct   1200
ccaggggaaa gagccaccct ctcctgcagg gccagtgaga gtgttagtag cgacttagcc   1260
tggtaccagc agaaacctgg ccaggctccc aggctcctca tatatggtgc atccaccagg   1320
gccaccggtg tcccagccag gttcagtggc agtgggtctg ggcagaatt cactctcacc   1380 atcagcagcc tgcagtctga agattttgca gtttattact gtcagcagta caataactgg   1440
```

<210> SEQ ID NO 5
<211> LENGTH: 127
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 5

```
cctccggagg tggcggtagt ggggggaggcg gttcaggcgg aggtggatcc ggaggcggag     60
ggtcgggcgg gggtggaagc gggggtggcg gctctggtgg cggaggtacc actagttaag    120
tgagtag                                                              127
```

<210> SEQ ID NO 6
<211> LENGTH: 39
<212> TYPE: PRT
<213> ORGANISM: Artificial Sequence
<220> FEATURE:
<223> OTHER INFORMATION: Description of Artificial Sequence: peptide
      encoded by SEQ ID NO: 5

<400> SEQUENCE: 6

```
Ala Ser Gly Gly Gly Gly Ser Gly Gly Gly Gly Ser Gly Gly Gly Gly
  1               5                  10                  15

Ser Gly Gly Gly Gly Ser Gly Gly Gly Gly Ser Gly Gly Gly Gly Ser
             20                  25                  30

Gly Gly Gly Gly Thr Thr Ser
         35
```

<210> SEQ ID NO 7
<211> LENGTH: 103
<212> TYPE: DNA
<213> ORGANISM: Artificial Sequence
<220> FEATURE:
<223> OTHER INFORMATION: Description of Artificial Sequence: primer

<400> SEQUENCE: 7

```
ttttatggat ccggtggcgg agggtcgggc gggggtggaa gcggggggtgg cggctccgga     60 ggcggaggtt cacaggtgca gctgctcgag tctggggctg agg                      103
```

```
<210> SEQ ID NO 8
<211> LENGTH: 32
<212> TYPE: PRT
<213> ORGANISM: Artificial Sequence
<220> FEATURE:
<223> OTHER INFORMATION: Description of Artificial Sequence: peptide
      encoded for by SEQ ID NO: 7

<400> SEQUENCE: 8

Gly Ser Gly Gly Gly Ser Gly Gly Gly Gly Ser Gly Gly Gly Gly
  1               5                  10                  15

Ser Gly Gly Gly Ser Gln Val Gln Leu Leu Glu Ser Gly Ala Glu
             20                  25                  30

<210> SEQ ID NO 9
<211> LENGTH: 65
<212> TYPE: DNA
<213> ORGANISM: Artificial Sequence
<220> FEATURE:
<223> OTHER INFORMATION: Description of Artificial Sequence: primer

<400> SEQUENCE: 9
taatttatcg atcacgtgac tagtcctagg cccgggtcaa tgatgatgat gatgatggcc      60
gctgc                                                                 65

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence:  peptide
      encoded for by SEQ ID NO: 9

<400> SEQUENCE: 10

Ser Gly His His His His His His
  1               5

<210> SEQ ID NO 11
<211> LENGTH: 131
<212> TYPE: DNA
<213> ORGANISM: Artificial Sequence
<220> FEATURE:
<223> OTHER INFORMATION: Description of Artificial Sequence: reverse
      oligonucleotide

<400> SEQUENCE: 11
ctagctactc acttaactag tggtacctcc gccacctgag ccgccacccc cgcttccacc      60
ccccgcccga ccctccgcct ccggatccac ctccgcctga accgcctccc cactaccgcc     120
acctccggag g                                                         131
```

CHIMERIC PROTEIN FOR PREVENTION AND TREATMENT OF HIV INFECTION

CROSS REFERENCE TO RELATED APPLICATIONS

This is a continuation of U.S. patent application Ser. No. 09/936,702, filed Sep. 13, 2001, now U.S. Pat. No. 7,115,262, issued Oct. 3, 2006, which is a National Stage of International Application No. PCT/US00/06946, filed Mar. 16, 2000, and claims the benefit of U.S. Provisional Application No. 60/124,681, filed Mar. 16, 1999, all of which are incorporated herein in their entirety.

FIELD OF THE INVENTION

This invention relates to proteins useful in the prevention and treatment of human immunodeficiency virus (HIV) infection. More specifically, it relates to fusion proteins that bind to two sites on a single target protein, especially when one binding domain of the fusion protein binds to an induced site (on the target protein) that is exposed by the binding of the other binding domain of the fusion protein.

BACKGROUND OF THE INVENTION

Acquired immune deficiency syndrome (AIDS) is a fatal disease of growing prevalence in the modern world. The agent responsible for this disease, human immunodeficiency virus (HIV), was first identified in 1983. HIV is a T-lymphotropic retrovirus that invades and replicates in cells of the immune system, primarily helper T-lymphocytes. The consequent dysfunction in T-lymphocyte-mediated immunity results in an immuno-compromised condition. Patients usually die of associated opportunistic viral, bacterial or fungal infections. A characteristics laboratory finding in AIDS is the decrease in helper T lymphocytes (CD4), and particularly a steady decrease in the ratio of CD4 to suppressor T lymphocytes CD8 as the disease progresses. Virus binding is primarily mediated by interaction of gp120, the external subunit of the HIV envelope glycoprotein (Env) with CD4 protein and various coreceptor molecules (one of several alternative chemokine receptors). These interactions then activate the gp41 transmembrane subunit of the envelope glycoprotein, to cause fusion between the virus and cell membranes. See *Retroviruses*, Coffin et al. (eds.) (1997) CSHP, New York, Ch. 11.

The humoral immune system is triggered by HIV infection, though it generally does not provide sufficient protection to ward off the infection. Env is the major target of anti-HIV neutralizing antibodies (Wyatt et al. *Nature* 393:705-711, 1998). However, Env has evolved so that its relatively invariant neutralizing determinants are protected from the humoral immune system. Antibodies to these regions therefore are generated at a low frequency and their neutralizing activities in vivo are generally weak. Certain variable regions (e.g., the V3 loop) are targets for potent neutralizing antibodies, but these are typically restricted to a limited number of HIV-strains (in other words, they are not broadly cross-reactive). For a list of several gp120 antigenic epitopes and consensus definitions of the conserved and variable regions of gp120, see published PCT application PCT/US98/02766 (publication number WO 98/36087) and Coffin et al. (eds.) (1997) CSHP, New York, Ch. 12.

A neutralizing monoclonal antibody (MAb) with potent and broadly cross-reactive activity would have great potential value in protocols aimed at preventing HIV infection before or immediately after exposure, for example in neonatal transmission, post-exposure prophylaxis, and as a topical inhibitor. Such a MAb may also be useful in treating chronic infection (D'Souza et al. *J. Infect. Dis.* 175:1056-1062, 1997). However only a handful of MAbs with the desired broadly cross-reactive neutralizing activities have been described. Because of limited potency and cross-reactivity of these molecules, even the three most promising candidates have questionable clinical value (D'Souza et al., 1997).

Extensive efforts are underway to provide immunological or pharmacological approaches to controlling HIV infection (Coffin et al., 1997, Ch. 12). The specific interaction between gp120 and CD4 has been exploited in efforts to provide a possible treatment for HIV infection. See, e.g., U.S. Pat. No. 5,817,767; Capon et al., *Nature* 337:525-531, 1989. A soluble fragment of CD4 (sCD4), comprising the first and second domains of this protein (D1D2) has been generated, and this molecule interacts specifically with gp120, essentially serving as a molecular decoy. sCD4 has been shown to block the spread of HIV between cultured cells (Moore et al., *Science* 250:1139-1142, 1990). However, clinical trials with sCD4 were inconclusive as to the effects on human viral load (Schooley et al., *Ann. Internal Med.* 112:247-253, 1990; Kahn et al., *Ann. Internal Med.* 112:254-261, 1990). Subsequent studies indicated that, unlike laboratory-adapted HIV strains, isolates obtained directly from infected patients (primary isolates) are resistant to neutralization by sCD4 (Darr et al., *Proc. Natl. Acad. Sci.* 87:6574-6578, 1990).

In another approach, researchers have generated an antibody-like molecule by fusing the binding portion of CD4 to the constant region (Fc) of a human IgG heavy chain (see, e.g., Capon et al., *Nature* 337:525-531, 1989; and Byrn et al., *Nature* 344:667-670, 1990). This molecule, termed CD4 immunoadhesin, exploits the native functions of immunoglobulin Fc, such as its ability to fix complement, its ability to mediate antibody-dependent cytotoxicity, and its transfer across the placental barrier. There are significant drawbacks to using Fc receptors in association with CD4, because such a construct may be responsible for targeting HIV to Fc-receptor bearing cells (e.g. macrophages), and might lead to increased transmission of HIV-1 across the placental barrier.

A complementary recombinant molecule has also been made, wherein the binding portion of CD4 is fused to the Fv region of an antibody directed to human CD3; this "Janusin" molecule may be able to re-target cytotoxic T-lymphocytes onto HIV-infected cells (Traunecker et al., *Embo J.* 10:3655-3659, 1991; Traunecker et al., *Int. J. Cancer: Supp.* 7:51-52, 1992). Janusin has been reported to inhibit HIV-mediated cell fusion when administered in vitro with neutralizing antibody to either gp41 or the V3 loop of gp120 (Allaway et al., *AIDS Res. Hum. Retroviruses* 9:581-587, 1993; U.S. Pat. No. 5,817, 767). This system is inherently complicated and inefficient because multiple molecules must be co-administered to the subject.

This invention is directed to proteins that address key failures of the prior art.

SUMMARY OF THE INVENTION

The present invention takes advantage of the finding that the neutralizing activities of MAbs against certain highly conserved determinants of the coreceptor-binding region of gp120 are revealed only when CD4 first binds to gp120 (as in an sCD4-activated fusion assay). Although some MAbs to CD4-induced epitopes (e.g., the human MAbs 17b and 48d, Thali et al., *J. Virol.* 67:3978-3988, 1993) are broadly cross-reactive with Envs from diverse HIV genetic subtypes (Clades), these neutralizing epitopes are only briefly exposed in vivo, and therefore have provided poor targets for clinically protective antibody binding.

The inventors have overcome these difficulties by creating a fusion protein containing a fragment of CD4 attached via a linker to a human single chain Fv directed against an induced (for example, a CD4-induced) neutralizing epitope on gp120, for instance a coreceptor-binding determinant of gp120. CD4-binding exposes highly conserved gp120 determinants involved in binding to coreceptor; therefore the provided fusion protein will have the properties of a highly potent, broadly cross-reactive neutralizing antibody with high in vivo activity and no Fc-mediated undesirable targeting properties. When the fusion protein is substantially derived from human proteins, it has minimal immunogenicity and toxicity in humans. Such an agent has great value in the prevention of infection during or immediately after HIV exposure (mother/infant transmission, post-exposure prophylaxis, topical inhibitor), and also in the treatment of chronic infection.

Accordingly, a first embodiment of the current invention is a neutralizing bispecific fusion protein capable of binding to two sites on a target protein. This protein has two different binding domains, an inducing-binding domain and an induced-binding domain, functionally linked by a peptide linker. Nucleic acid molecules encoding such fusion proteins are further aspects of this invention. Also encompassed in the invention are protein analogs, derivatives, or mimetics of such neutralizing bispecific fusion proteins. The arrangement of the inducing- and induced-binding domains need not be organized in binding sequence; the amino-proximal or carboxy-proximal binding domain of the fusion protein may be either the induced-binding or the inducing-binding domain.

In certain embodiments, the linker of this invention is of such length and secondary structure that the linker allows the second binding domain to be in binding proximity to the induced epitope of the target protein when the first binding domain is bound to the inducing site of the target protein. The linker may for instance be substantially flexible. Linkers of about 25-100 angstroms (Å), or about 15-100 amino acid residues in length, are examples of linkers of a sufficient length to maintain the second binding domain in binding proximity to the induced epitope. Specific examples of linkers will include one or more occurrences of the amino acid sequence represented by SEQ ID NO: 1. For instance, the invention encompasses bispecific fusion proteins wherein the two binding domains are functionally linked by the amino acid sequence represented by SEQ ID NO: 2.

Targets for bispecific fusion proteins according to this invention include viral envelope proteins. For instance, viral envelope proteins from the human immunodeficiency virus (HIV) are targets for the disclosed invention. In a specific embodiment of the invention, the viral envelope protein target is gp120.

In further aspects of the invention, the first binding domain is capable of binding to an inducing site on the target protein, thereby exposing an induced epitope. For instance, the first binding domain can be a ligand such as CD4 or fragments thereof. Alternatively, such a first binding domain may be a binding portion of a variable region of an antibody heavy or light chain. The first binding domain may include, for example, an antibody-binding domain, a single-chain Fv (SCFv), or binding fragments thereof.

The second binding domain, which is capable of forming a neutralizing complex with an induced epitope of the target protein, may be for example an antibody or fragments thereof, such as the variable region, Fv, Fab or antigen-binding domain of an antibody. Another example of the second binding domain of the fusion protein is an engineered single-chain Fv (SCFv).

In some particular examples where HIV gp120 is the target, and the inducing site is the gp120 CD4 binding site, the induced epitope may be a coreceptor-binding determinant of gp120. Accordingly, aspects of this invention include proteins in which the first binding domain binds to gp120 in such a way as to cause a CD4-induced conformational change in the complexed gp120 that exposes the second binding domain. The first binding domain may be derived from a CD4 molecule, and include CD4 and soluble fragments thereof (sCD4, e.g. D1, D1D2 and other such fragments), and proteins that mimic the biological activity of a CD4 molecule in binding to the inducing site of gp120. In another embodiment of the invention, the first domain of the gp120-targeted bispecific fusion protein is derived from a CD4 anti-idiotypic antibody, or antibodies that mimic CD4 in exposing epitopes.

The second domain of the gp120-targeted bispecific fusion protein, which binds to an epitope induced by binding of the first fusion domain, may be chosen from domains and fragments of proteins that bind to such CD4 induced epitopes. Antibodies directed to the induced epitopes, as well as the HIV coreceptor (e.g. a chemokine receptor), HIV coreceptor mimics, and fragments of HIV coreceptor proteins, are examples of sources for the second binding domain of a gp120-target bispecific fusion protein of this invention. Examples of chemokine receptors with HIV coreceptor activity include CXCR4, CCR5, CCR2B, and CCR3. Neutralizing antibodies, including 17b and 48d, are examples of antibodies. Fusion proteins wherein the second domain is an engineered single chain Fv (SCFv) derived from such a neutralizing antibody are also encompassed.

A particular embodiment of this invention is a functional recombinant bispecific fusion protein capable of binding to two sites on gp120, wherein the inducing-binding domain is sCD4; the induced-binding domain is SCFv(17b); and these two domains are linked by a linker of a length sufficient to maintain the SCFv(17b) in binding proximity an SCFv(17b) epitope when sCD4 is bound to gp120. A prototypical bispecific fusion protein has the amino acid sequence shown in SEQ ID NO: 3. Nucleic acid molecules encoding such a fusion protein are also encompassed; the prototypical nucleic acid molecule has the sequence shown in SEQ ID NO: 4. Vectors and cells comprising this nucleic acid molecule are also encompassed in the current invention, as are transgenic plants and animals that express the nucleic acid molecule.

This invention also provides methods for producing functional recombinant bispecific fusion proteins capable of binding two sites on a target protein. Such a protein can be produced in a prokaryotic or eukaryotic cell (e.g., yeast, insect and mammalian cells), for instance by transforming or transfecting such a cell with a recombinant nucleic acid molecule comprising a sequence which encodes a disclosed bispecific fusion protein. Such transformed cells can then be cultured under conditions that cause production of the fusion protein, which is then recovered through protein purification means. The protein can include a molecular tag, such as a six-histidine tag, to facilitate its recovery. In particular embodiments, the protein has a hexa-histidine (hexa-his) tag, and a thrombin cleavage site.

The invention further provides methods for inactivating a target protein, for instance a gp120 protein, by contacting the target protein with a fusion protein according to this invention. Where the target protein is gp120, this method involves contacting gp120 with a gp120-targeted bispecific fusion protein, for instance sCD4-SCFv(17b). Proteins according to the current invention can also be used to neutralize a human immunodeficiency virus, by contacting the human immunodeficiency virus with a gp120-targeted fusion protein according to this invention. Binding of a viral or recombinant gp120 protein to soluble CD4 or lymphocyte CD4 can also be blocked and/or prevented by contacting the gp120 protein with gp120-targeted fusion protein. In any of these methods, a variant protein, analog or mimetic of the fusion protein as provided herein may also be used.

Proteins of the current invention can be used to inhibit virus replication or infectivity in a subject by administering to the subject an amount of the fusion protein (for example the sCD4-SCFv(17b) fusion protein), or a variant protein, analog or mimetic thereof, sufficient to inhibit HIV virus replication or infectivity. The fusion protein can be administered in a pharmaceutical composition, and given therapeutically to a person who is known to be infected with HIV, or prophylactically to help prevent infection in someone who has been exposed to the virus, or is at high risk for exposure. Proteins of this invention can also be administered in combination with another compound for the treatment or prevention of HIV infection, such as an HIV reverse transcriptase (RT), integrase, or protease inhibitor, another HIV-1 neutralizing antibody, or an Env-targeted toxin. The other drug may be an HIV antiviral agent, an HIV anti-infective agent, and/or an immunomodulator, or combinations thereof.

BRIEF DESCRIPTION OF THE FIGURES

FIGS. 4A, 4B, and 4C depict the proposed interaction of HIV (mediated by gp120) with the cell surface receptor CD4 and co-receptor CCR5, and the beginning of fusion (mediated by gp41). Interaction between gp120 and CD4 (FIG. 4A) causes a change in the conformation of gp120 (FIG. 4B), which enables interaction between gp120 and CCR5 (FIG. 4B). This triggers a conformational change in gp41 (FIG. 4C), and leads to fusion. Antibody (for instance, MAb 17b) binds poorly to the transiently exposed epitope on gp120 (FIG. 4B), and thus results in only weak neutralization of fusion or infection.

FIGS. 4D and 4E depict a proposed mechanism of sCD4-SCFV(17b) neutralization of fusion. In the presence of the bispecific chimeric fusion protein, the sCD4 domain can bind to gp120 and induce a conformational change in this protein sufficient to permit binding of the SCFV(17b) (FIG. 4D). This effectively blocks fusion between the HIV and infection and the target cell.

SEQUENCE LISTING

Figure 1:
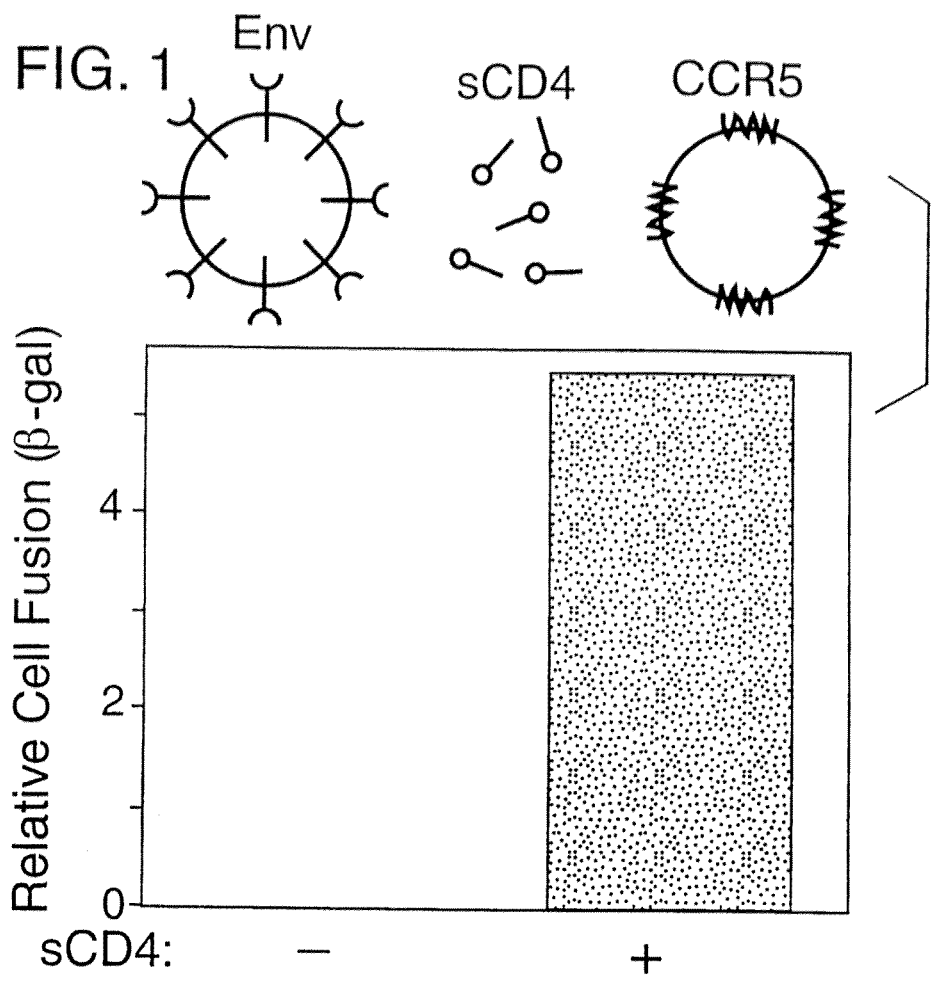
FIG. 1 is a bar graph illustrating relative HIV-1 Env-mediated fusion, in the presence (+) or absence (−) of soluble CD4, between effector cells expressing Env (Ba-L) and target cells expressing CCR5 (co-receptor), but no CD4 (primary receptor).
Figure 2:
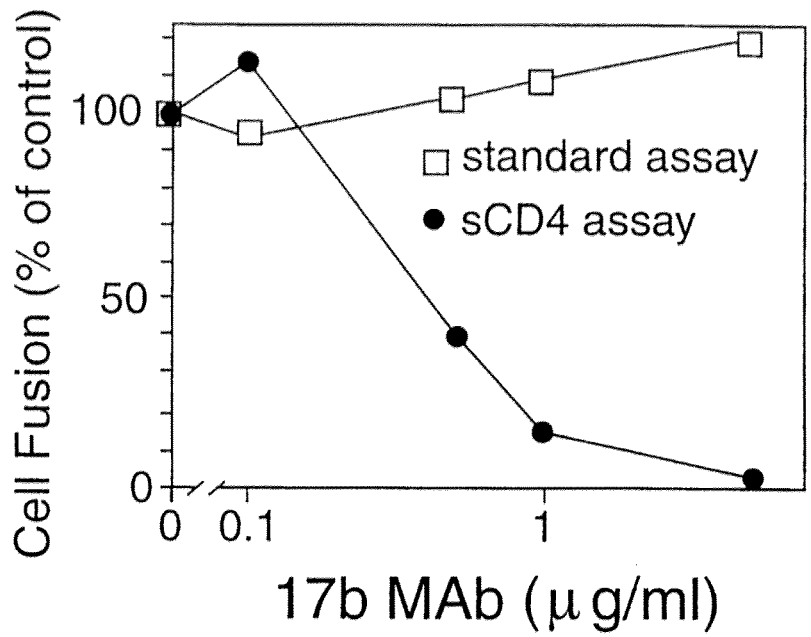
FIG. 2 is a graph showing that antibody 17b does not inhibit HIV-1 Env-mediated fusion in the conventional assay (open box: CXCR4 and CD4 on target cell), but strongly inhibits cell fusion in the sCD4-activated assay (filled circle: only CXCR4 on target cell, sCD4 provided). Additional experiments indicate that this phenomenon occurs with diverse Envs using either CXCR4 or CCR5, and that 17b has broad cross-reactive activity with Envs from genetically diverse HIV-1 isolates.

The nucleic and amino acid sequences listed in the accompanying sequence listing are shown using standard letter abbreviations for nucleotide bases, and three letter code for amino acids. Only one strand of each nucleic acid sequence is shown, but the complementary strand is understood as included by any reference to the displayed strand.

SEQ ID NO: 1 shows the basic repeat cassette for a linker polypeptide.

SEQ ID NO: 2 shows a seven-repeat polypeptide linker

SEQ ID NO: 3 shows the amino acid sequence of the CD4-SCFv(17b) chimeric protein.

SEQ ID NO: 4 shows the nucleic acid sequence of CD4-SCFv(17b).

SEQ ID NO: 5 shows the pair of synthetic oligonucleotides used to form the second half of the Stu I site near the 3' end of CD4 and to produce an Spe I overhang at the 3' end of an intermediate construct (site to be destroyed upon ligation into pCB-3); the oligonucleotide sequences reconstruct the remainder of the second domain of CD4 (through ser$_{183}$), and encode an amino acid sequence including ala$_{182}$ser$_{183}$ of CD4 D2 plus an intermediate 37 residue linker (gly$_4$ser)$_6$gly$_4$thr$_2$ser, followed directly by the universal translational termination sequence (UTS).

SEQ ID NO: 6 shows the peptide sequence encoded for by the nucleotide sequences in SEQ ID NO: 5.

SEQ ID NO: 7 shows the forward (5') primer used to amplify and attach the 17b SCFv sequence to the CD4-linker sequence in pCD2. Italics show the region of the primer that overlaps with 17b.

SEQ ID NO: 8 shows the amino acid sequence encoded by the oligonucleotide primer in SEQ ID NO:7. This sequence includes the GlySer residues at the third (Gly$_4$Ser) repeat within L1 (encoded by the BamH I site, followed by the remaining four (Gly$_4$Ser) repeats, followed by the first ten residues of the 17b SCFv (shown in italics).

SEQ ID NO: 9 shows the 3' primer used to amplify and attach the 17b SCFv sequence plus the thrombin cleavage site and the hexa-his tag to the CD4-linker sequence in pCD2.

SEQ ID NO: 10 shows the peptide encoded for by the nucleotide sequence in SEQ ID NO: 9.

DETAILED DESCRIPTION OF THE INVENTION

I. Abbreviations and Definitions

A. Abbreviations

HIV: human immunodeficiency virus
gp120: the external subunit of the envelope glycoprotein complex of HIV
Env: the envelope glycoprotein complex of HIV
MAb: monoclonal antibody
Fv: antibody "fragment variable", the variable region of an antibody
SCFv: single-chain antibody variable region

B. Definitions

Unless otherwise noted, technical terms are used according to conventional understanding. Definitions of common terms in molecular biology may be found in Benjamin Lewin, *Genes V*, Oxford University Press, 1994 (ISBN 0-19-854287-9); Kendrew et al. (eds.), *The Encyclopedia of Molecular Biology*, Blackwell Science Ltd., 1994 (ISBN 0-632-02182-9); and Robert A. Meyers (ed.), *Molecular Biology and Biotechnology: a Comprehensive Desk Reference*, VCH Publishers, Inc., 1995 (ISBN 1-56081-569-8).

In order to facilitate review of the various embodiments of the invention, the following definitions of terms are provided:

Animal: Living multi-cellular vertebrate organisms, a category that includes, for example, mammals and birds. The term mammal includes both human and non-human mammals. Similarly, the term "subject" includes both human and veterinary subjects.

Bispecific fusion protein: Proteins that have at least two domains fused together, each domain comprising a binding region capable of forming a specific complex with a target protein. In general, the two domains are genetically fused together, in that nucleic acid molecules that encode each protein domain are functionally linked together, for instance by a linker oligonucleotide, thereby producing a single fusion-encoding nucleic acid molecule. The translated product of such a fusion-encoding nucleic acid molecule is the bispecific fusion protein.

The two binding regions of such a bispecific protein may associate with two different binding determinants or epitopes on a single target molecule. One binding domain may bind first to such a target and thereby induce a conformational change in the target such that the binding of the second binding domain to the target is enabled, facilitated, or otherwise increased in affinity. In such an instance, the domain that binds first to the target can be referred to as the inducing-binding domain, while the domain that binds second is the induced-binding domain. These fusion protein domains need not be organized in binding sequence; the amino-proximal binding domain of the fusion protein may be either the induced-binding or the inducing-binding domain; likewise for the carboxy-proximal binding domain.

Bispecific fusion proteins can be further labeled according to the target protein they bind to and neutralize. For instance, a bispecific fusion protein according to the current invention that binds to two specific sites on HIV gp120 protein may be referred to as a gp120-targeted bispecific fusion protein.

CD4: Cluster of differentiation factor 4, a T-cell surface protein that mediates interaction with the MHC class II molecule. CD4 also serves as the primary receptor site for HIV on T-cells during HIV infection.

Molecules that are derived from CD4 include fragments of CD4, generated either by chemical (e.g. enzymatic) digestion or genetic engineering means. Such a fragment may be one or more entire CD4 protein domains (for example, extracellular domains D1, D2, D3, and D4), as defined in the immunological literature, or a portion of one or more of these well-defined domains. For instance, a binding molecule or binding domain derived from CD4 would comprise a sufficient portion of the CD4 protein to mediate specific and functional interaction between the binding fragment and a native or viral binding site of CD4. One such binding fragment includes both the D1 and D2 extracellular domains of CD4 (CD4 D1D2), though smaller fragments may also provide specific and functional CD4-like binding. The gp120-binding site has been mapped to D1 of CD4.

The term "CD4-derived molecules" also encompasses analogs (non-protein organic molecules), derivatives (chemically functionalized protein molecules obtained starting with the disclosed protein sequences) or mimetics (three-dimensionally similar chemicals) of the native CD4 structure, as well as proteins sequence variants or genetic alleles, that maintain the ability to functionally bind to a target molecule.

CD4-induced conformational change: A change induced in the three-dimensional conformation of the interacting gp120 protein when CD4 specifically interacts with gp120 to form a complex. One characteristic of such a change is the exposure of at least one induced epitope on the interacting gp120 molecule. An epitope induced by such a change is called a CD4-induced epitope. Such a CD4-induced epitope may for instance include gp120 epitopes at or near the co-receptor-binding region of the protein.

In addition to CD4 binding, the binding of other molecules may induce the exposure of induced epitopes on gp120. Such other inducing molecules are considered CD4-like in terms of their epitope-inducing ability, to the extent that they expose epitopes congruent with or equivalent to those induced epitopes exposed upon the binding of native CD4. These other inducing molecules include, but in no way are limited to, fragments of CD4, for instance sCD4, or a fragment containing the D1 or D1 and D2 domains of native CD4. A mannose-specific lectin (SC) may also serve to expose a CD4-induced epitope (see U.S. Pat. No. 5,843,454), as can certain anti-gp120 MAbs.

Complex (complexed): Two proteins, or fragments or derivatives thereof, are said to form a complex when they measurably associate with each other in a specific manner. Such association can be measured in any of various ways, both direct and indirect. Direct methods may include co-migration in non-denaturing fractionation conditions, for instance. Indirect measurements of association will depend on secondary effects caused by the association of the two proteins or protein domains. For instance, the formation of a complex between a protein and an antibody may be demonstrated by the antibody-specific inhibition of some function of the target protein. In the case of gp120, the formation of a complex between gp120 and a neutralizing antibody to this protein can be measured by determining the degree to which the antibody inhibits gp120-dependent cell fusion or HIV infectivity. Cell fusion inhibition and infectivity assays are discussed further below.

Exposing an induced epitope: The process by which two proteins interact specifically to form a complex (an inducing complex), thereby causing a conformational change in at least one of the two proteins (the target protein) such that at least one previously poorly accessible epitope (an induced epitope) is made accessible to intramolecular interaction. The formation of such an inducing complex will generally cause the exposure of more than one induced epitope, each of which may be thereby rendered accessible for intramolecular interaction.

HIV coreceptor: A cell-surface protein other than CD4 involved in the interaction of HIV virus and its subsequent entry into a target cell. These proteins may also be referred to as fusion coreceptors for HIV. Examples of such coreceptor proteins include, for instance, members of the chemokine receptor family (e.g. CXCR4, CCR5, CCR3, and CCR2B).

HIV coreceptor proteins interact with coreceptor binding determinants of gp120. In general, it is believed that some of these determinants are exposed on gp120 only after the specific interaction of gp120 with CD4, and the consequent CD4-induced conformational change in the interacting gp120. Thus certain HIV coreceptor binding determinants are, or overlap with, CD4-induced epitopes.

Neutralization of gp120 can be achieved by the specific binding of neutralizing proteins or protein fragments or domains to one or more coreceptor binding determinants of gp120, thereby blocking interaction between complexed gp120 and the native coreceptor.

HIV neutralizing ability: The measurable ability of a molecule to inhibit infectivity of HIV virus, either in vivo or in vitro. The art is replete with methods for measuring the neutralizing ability of various molecules. Techniques include in vitro peripheral blood mononuclear cell (PBMC) based assays (D'Souza et al., 1997); measurement of virion attachment (Mondor et al., *J. Virol.* 72:3623-3634, 1998); neutral red dye uptake and antigen capture assays (U.S. Pat. No. 5,695,927); vaccinia-based reporter gene cell fusion assay (Nussbaum et al., *J. Virol.* 68:5411-5422, 1994) (standard and sCD4 activated assays); productive infection assays (measuring gag antigen p24 or RT synthesis) (Karn, *HIV: a practical approach.* Oxford Univ. Press, Cambridge, 1995); and infectivity titer reduction assays (Karn, 1995).

In addition, physical interaction between gp120 and CD4 or other CD4-like molecules can be examined by various methods. See, for instance U.S. Pat. No. 5,843,454 (measuring conformational changes of gp120 on binding of various proteins by virus release and susceptibility of gp120 to thrombin-mediated cleavage of the V3 loop). Alternately, the ability of the CD4-like molecule to compete for binding to gp120 with either native CD4 or antibody that recognizes the CD4 binding site on gp120 (CD4BS) can be measured. This will allow the calculation of relative binding affinities through standard techniques.

The invention also includes analogs, derivatives or mimetics of the disclosed fusion proteins, and which have HIV neutralizing ability. Such molecules can be screened for HIV neutralizing ability by assaying a protein similar to the disclosed fusion protein, in that it has one or more conservative amino acid substitutions, or analogs, derivatives or mimetics thereof, and determining whether the similar protein, analog, derivative or mimetic provides HIV neutralization. The HIV neutralization ability and gp120 binding affinity of these derivative compounds can be measured by any known means, including those discussed in this application Injectable composition: A pharmaceutically acceptable fluid composition comprising at least one active ingredient, e.g. a bispecific fusion protein. The active ingredient is usually dissolved or suspended in a physiologically acceptable carrier, and the composition can additionally comprise minor amounts of one or more non-toxic auxiliary substances, such as emulsifying agents, preservatives, and pH buffering agents and the like. Such injectable compositions that are useful for use with the fusion proteins of this invention are conventional; formulations are well known in the art.

Isolated: An "isolated" biological component (such as a nucleic acid molecule, protein or organelle) is one that has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Neutralizing antibodies: An antibody that is able to specifically bind to a target protein in such a way as to inhibit the subsequent biological functioning of that target protein is said to be neutralizing of that biological function. In general, any protein that can perform this type of specific blocking activity is considered a neutralizing protein; antibodies are therefore a specific class of neutralizing protein. The complex formed by binding of a neutralizing protein to a target protein is called a neutralizing complex.

Antibodies that bind to viruses and bacteria and thereby prevent the binding of these pathogens to target host cells are said to neutralize the pathogen. Therefore, antibodies that bind to HIV proteins and measurably reduce the ability of the virus to bind to or enter target cells (e.g., T-cells or macrophages) are HIV-neutralizing antibodies. In general, HIV neutralizing antibodies can be broken down into several different classes dependent on what region of the viral envelope protein the antibody binds to. Broad classes of such antibodies include anti-gp41 and anti-gp120 antibodies. There are several antigenic regions on the gp120 protein that provide epitopes for the natural or laboratory generation of HIV neutralizing antibodies (see WO 98/36087). Broadly cross-reactive neutralizing antibodies usually interact with relatively invariant regions of Env.

A primary source of neutralizing antibodies is the peripheral blood of patients infected with the HIV virus. Such primary isolates can be cloned and/or immortalized using standard techniques. In addition to the isolation of naturally-occurring neutralizing antibodies, procedures specifically directed toward their production are known in the art. See U.S. Pat. Nos. 5,843,454; 5,695,927; 5,643,756; and 5,013, 548 for instance.

Linker: A peptide, usually between two and 150 amino acid residues in length that serves to join two protein domains in a multi-domain fusion protein. Examples of specific linkers can be found, for instance, in Hennecke et al. (*Protein Eng.* 11:405-410, 1998); and U.S. Pat. Nos. 5,767,260 and 5,856, 456.

Depending on the domains being joined, and their eventual function in the fusion protein, linkers may be from about two to about 150 amino acids in length, though these limits are given as general guidance only. The tendency of fusion proteins to form specific and non-specific multimeric aggregations is influenced by linker length (Alfthan et al., 1998 *Protein Eng.* 8:725-731, 1998). Thus, shorter linkers will tend to promote multimerization, while longer linkers tend to favor maintenance of monomeric fusion proteins. Aggregation can also be minimized through the use of specific linker sequences, as demonstrated in U.S. Pat. No. 5,856,456.

Linkers may be repetitive or non-repetitive. One classical repetitive linker used in the production of single chain Fvs (SCFvs) is the $(Gly_4Ser)_3$ (or $(GGGGS)_3$ or $(G_4S)_3$) linker. More recently, non-repetitive linkers have been produced, and methods for the random generation of such linkers are known (Hennecke et al., *Protein Eng.* 11:405-410, 1998). In addition, linkers may be chosen to have more or less secondary character (e.g. helical character, U.S. Pat. No. 5,637,481) depending on the conformation desired in the final fusion protein. The more secondary character a linker possesses, the more constrained the structure of the final fusion protein will be. Therefore, substantially flexible linkers that are substantially lacking in secondary structure allow flexion of the fusion protein at the linker.

A linker is capable of retaining a binding domain of a protein in binding proximity of a target binding site when the linker is of sufficient length and flexibility to allow specific interaction between the binding domain and the target binding site. In the case of the bispecific fusion proteins of this invention, a linker that maintains binding proximity permits the sequential binding with the target of first the inducing-binding domain of the fusion protein, then the induced-binding domain. A linker that maintains the domains of a bispecific fusion protein in binding proximity to a target can be considered an operable or functional linker as relates to such a bispecific fusion protein.

Oligonucleotide: A linear polynucleotide sequence of between six and 300 nucleotide bases in length.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

ORF (open reading frame): A series of nucleotide triplets (codons) coding for amino acids without any internal termination codons. These sequences are usually translatable into a peptide.

Parenteral: Administered outside of the intestine, e.g., not via the alimentary tract. Generally, parenteral formulations are those that will be administered through any possible mode except ingestion. This term especially refers to injections, whether administered intravenously, intrathecally, intramuscularly, intraperitoneally, or subcutaneously, and various surface applications including intranasal, intradermal, and topical application, for instance.

Pharmaceutically acceptable carriers: The pharmaceutically acceptable carriers useful in this invention are conventional. Remington's Pharmaceutical Sciences, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Purified: The term purified does not require absolute purity; rather, it is intended as a relative term. Thus, for example, a purified fusion protein preparation is one in which the fusion protein is more enriched than the protein is in its generative environment, for instance within a cell or in a biochemical reaction chamber. In some embodiments, a preparation of fusion protein is purified such that the fusion protein represents at least 50% of the total protein content of the preparation.

Recombinant: A recombinant nucleic acid molecule is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

Similarly, a recombinant protein is one encoded for by a recombinant nucleic acid molecule.

Sequence identity: The similarity between two nucleic acid sequences, or two amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs of the bispecific fusion protein will possess a relatively high degree of sequence identity when aligned using standard methods.

Methods of alignment of sequences for comparison are well known in the art. Various programs and alignment algorithms are described in: Smith and Waterman (Adv. Appl. Math. 2: 482, 1981); Needleman and Wunsch (J. Mol. Biol. 48: 443-453, 1970); Pearson and Lipman (Proc. Natl. Acad. Sci., USA 85:2444-2448, 1988); Higgins and Sharp (Gene, 73:237-244, 1988); Higgins and Sharp (CABIOS 5:151-153, 1989); Corpet et al. (Nuc. Acids Res. 16: 10881-10890, 1988); Huang et al. (Comp. Appls. Biosci. 8:155-165, 1992); and Pearson et al. (Methods in Molecular Biology 24: 307-331, 1994). Altschul et al. (Nature Genet., 6:119-129, 1994) presents a detailed consideration of sequence alignment methods and homology calculations.

The alignment tools ALIGN (Myers and Miller, CABIOS 4:11-17, 1989) or LFASTA (Pearson and Lipman, Proc. Natl. Acad. Sci., USA 85:2444-2448, 1988) may be used to perform sequence comparisons (Internet Program © 1996, W. R. Pearson and the University of Virginia, "fasta20u63" version 2.0u63, release date December 1996). ALIGN compares entire sequences against one another, while LFASTA compares regions of local similarity. These alignment tools and their respective tutorials are available on the Internet.

Orthologs of the disclosed bispecific fusion proteins are typically characterized by possession of greater than 75% sequence identity counted over the full-length alignment with the amino acid sequence of bispecific fusion protein using ALIGN set to default parameters.

The NCBI Basic Local Alignment Search Tool (BLAST) (Altschul et al., J Mol Biol. 1990 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI BLAST website. A description of how to determine sequence identity using this program is also available at the NCBI website BLAST tutorial.

For comparisons of amino acid sequences of greater than about 30 amino acids, the "Blast 2 sequences" function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 90%, at least 92%, at least 94%, at least 95%, at least 97%, at least 98%, or at least 99% sequence identity. In addition, sequence identity can be compared over the full length of one or both binding domains of the disclosed fusion proteins. In such an instance, percentage identities will be essentially similar to those discussed for full-length sequence identity.

When significantly less than the entire sequence is being compared for sequence identity, homologs will typically possess at least 80% sequence identity over short windows of 10-20 amino acids, and may possess sequence identities of at least 85%, at least 90%, at least 95%, or at least 99% depending on their similarity to the reference sequence. Sequence identity over such short windows can be determined using LFASTA; methods are described on the Internet. One of skill in the art will appreciate that these sequence identity ranges are provided for guidance only; it is entirely possible that strongly significant homologs could be obtained that fall outside of the ranges provided. The present invention provides not only the peptide homologs that are described above, but also nucleic acid molecules that encode such homologs.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found in Sambrook et al. (In *Molecular Cloning: A Laboratory Manual*, Cold Spring Harbor, N.Y., 1989) and Tijssen (*Laboratory Techniques in Biochemistry and Molecular Biology* Part I, Ch. 2, Elsevier, N.Y., 1993). Nucleic acid molecules that hybridize under stringent conditions to the disclosed bispecific fusion protein sequences will typically hybridize to a probe based on either the entire fusion protein encoding sequence, an entire binding domain, or other selected portions of the encoding sequence under wash conditions of 0.2×SSC, 0.1% SDS at 65° C.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences, each encoding substantially the same protein.

Specific binding agent: An agent that binds substantially only to a defined target. Thus a gp120-specific binding agent binds substantially only the gp120 protein. As used herein, the term "gp120-specific binding agent" includes anti-gp120 antibodies and other agents that bind substantially only to a gp120 protein.

Anti-gp120 antibodies may be produced using standard procedures described in a number of texts, including Harlow and Lane (*Using Antibodies, A Laboratory Manual*, CSHL, New York, 1999, ISBN 0-87969-544-7). In addition, certain techniques may enhance the production of neutralizing antibodies (U.S. Pat. Nos. 5,843,454; 5,695,927; 5,643,756; and 5,013,548). The determination that a particular agent binds substantially only to gp120 protein may readily be made by using or adapting routine procedures. One suitable in vitro assay makes use of the Western blotting procedure (described in many standard texts, including Harlow and Lane, 1999). Western blotting may be used to determine that a given protein binding agent, such as an anti-gp120 monoclonal antibody, binds substantially only to the MSG protein. Antibodies to gp120 are well known in the art.

Shorter fragments of antibodies can also serve as specific binding agents. For instance, FAbs, Fvs, and single-chain Fvs (SCFvs) that bind to gp120 would be gp120-specific binding agents.

Therapeutically effective amount of a bispecific fusion protein: A quantity of bispecific fusion protein sufficient to achieve a desired effect in a subject being treated. For instance, this can be the amount necessary to inhibit viral proliferation or to measurably neutralize disease organism binding mechanisms. In general, this amount will be sufficient to measurably inhibit virus (e.g. HIV) replication or infectivity.

An effective amount of bispecific fusion protein may be administered in a single dose, or in several doses, for example daily, during a course of treatment. However, the effective amount of fusion protein will be dependent on the fusion protein applied, the subject being treated, the severity and type of the affliction, and the manner of administration of the fusion protein. For example, a therapeutically effective amount of fusion protein can vary from about 0.01 mg/kg body weight to about 1 g/kg body weight.

The fusion proteins disclosed in the present invention have equal application in medical and veterinary settings. Therefore, the general term "subject being treated" is understood to include all animals (e.g. humans, apes, dogs, cats, horses, and cows) that are or may be infected with a virus or other disease-causing microorganism that is susceptible to bispecific fusion protein-mediated neutralization.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

II. Construction, Expression, and Purification of Bispecific Fusion Proteins

A. Selection of Component Domains

This invention provides generally a bispecific fusion protein that binds to two different sites on a target protein. As such, any target protein that has two different binding sites is an example of a target for a bispecific fusion protein. Particular targets include proteins on which one of the two binding sites (the induced-binding site) is exposed/induced by the binding of the fusion protein to a first binding site (the inducing-binding site) on the target. The choice of protein binding domains for incorporation into the disclosed bispecific fusion protein will be dictated by the target protein chosen. The choice of linker will also be influenced by the target protein and binding sites chosen. In general, the linker used in any bispecific fusion will be of a length and secondary character to hold the induced-binding domain within binding proximity of the target protein induced binding site, once the inducing-binding domain of the fusion protein has formed a specific complex with the target.

In certain embodiments, the target protein is an HIV envelope glycoprotein, for instance HIV-1 gp120. In certain of these and other embodiments, the inducing-binding site is the CD4 binding site on gp120. As such, the inducing-binding domain of the disclosed bispecific fusion protein can be a binding fragment of CD4, for instance sCD4. Alternately, any other molecule that specifically interacts with gp120 in such a way as to expose one or more induced epitopes would also serve as the source of an inducing-binding protein domain. The specific fragments used to construct the fusion protein should be chosen so that the conformation of the final fusion provides functional and inducing binding to gp120; this can be assayed either directly (e.g., affinity measurements) or indirectly (e.g., neutralization assays).

Non-CD4-derived CD4 mimics may also be employed as sources for inducing-binding domains of the disclosed fusion proteins. For instance, a mannose-specific lectin (SC) may serve to induce CD4 induced conformational changes (see U.S. Pat. No. 5,843,454). Alternatively, antibodies that bind the CD4-binding site or another epitope of gp120 and thereby induce a CD4-like conformational change on the complexed protein can also be used.

Non-peptide CD4 analogs can also be used in this invention, for instance organic or non-organic structural analog of the gp120-interacting domain(s) of the CD4 molecule.

Induced-binding domains of a gp120-targeted fusion protein will include antibodies (or fragments thereof) that recognize induced epitopes of the complexed gp120. In some embodiments, such antibodies are broadly cross-reactive against diverse HIV-1 isolates. Induced epitopes include all of those referred to as CD4-induced (CD4i) epitopes, and in particular those which overlap coreceptor-binding determinants of gp120. Previously identified neutralizing monoclonal antibodies can be used, and include but are not limited to human monoclonal antibodies 17b, 48d, and CG10.

Likewise, induced binding domains of the disclosed chimeric molecules can be non-peptide molecules, for instance organic or non-organic structural analogs of SCFv(17b).

In addition to antibodies that bind induced epitopes of gp120, other sources for induced-binding domains include fragments of coreceptors that specifically interact with a coreceptor binding domain(s) of gp120.

The construction of a gp120-specific bispecific fusion protein can be aided by review of the X-ray crystallographic structure of the ternary complex containing the gp120 core, a two-domain fragment of CD4 (D1D2), and an FAb from a broadly cross-reactive human MAb (17b) directed against the coreceptor-binding determinants of gp120 (Kwong et al., *Nature* 393:648-659, 1998). Computer-based examination of the structural coordinates of this ternary complex, using FRODO (Jones et al., *Meth. Enzymol.* 115:157-171, 1985; Jones, *J. Appl. Cryst.* 11:268-272, 1978; Pflugrath et al. Methods and Applications in Crystallography, pages 407-420, Clarendon Press, Oxford), has revealed choices for constructing the chimeric protein. The shortest distance between free termini of CD4 and the 17b FAb is 56 Å, i.e. from the free C-terminus of the D1D2 sCD4 fragment to the N-terminus of the 17b FAb heavy chain. A linker connecting these termini would be essentially free of steric hindrance from CD4 and the N-terminus of the 17b light chain. Possible connections could also be made between the N-terminus of CD4 and the C-termini of the 17b heavy or light chains; such connections would require linkers of about 65 Å and about 86 Å, respectively. In the latter two connections the linker is required to circumvent other portions of the complex, including the bulky variable loops.

B. Assembly

The construction of chimeric molecules, in particular fusion proteins, from domains of known proteins is well known. In general, a nucleic acid molecule that encodes the desired protein domains are joined using standard genetic engineering techniques to create a single, operably linked fusion oligonucleotide. Molecular biological techniques may be found in Sambrook et al. (In *Molecular Cloning: A Laboratory Manual*, Cold Spring Harbor, New York, 1989). Specific examples of genetically engineered multi-domain proteins, especially those based on molecules of the immunoglobulin superfamily, joined by various linkers, can be found in the following patent documents:

U.S. Pat. No. 5,856,456 ("Linker for linked fusion polypeptides");

U.S. Pat. No. 5,696,237 ("Recombinant antibody-toxin fusion protein");

U.S. Pat. No. 5,767,260 ("Antigen-binding fusion proteins");

U.S. Pat. No. 5,587,455 ("Cytotoxic agent against specific virus infection"); and WO 98/36087 ("Immunological tolerance to HIV epitopes").

Non-peptide analogs that serve as inducing-binding or induced binding domains of the invention can be linked to the opposite domain of the chimeric molecules using known chemical linking techniques, including chemical cross-linking. Cross-linkers are well known, and examples of molecules used for cross-linking can be found, for instance, in U.S. Pat. No. 6,027,890 ("Methods and compositions for enhancing sensitivity in the analysis of biological-based assays").

C. Expression

One skilled in the art will understand that there are myriad ways to express a recombinant protein such that it can subsequently be purified. In general, an expression vector carrying the nucleic acid sequence that encodes the desired protein will be transformed into a microorganism for expression. Such microorganisms can be prokaryotic (bacteria) or eukaryotic (e.g., yeast). One example species of bacteria that can be used is *Escherichia coli* (*E. coli*), which has been used extensively as a laboratory experimental expression system. An eukaryotic expression system can be used where the protein of interest requires eukaryote-specific post-translational modifications such as glycosylation. Also, protein can be expressed using a viral (e.g., vaccinia) based expression system.

Protein can also be expressed in animal cell tissue culture, and such a system can be used where animal-specific protein modifications are desirable or required in the recombinant protein.

The expression vector can include a sequence encoding a targeting peptide, positioned in such a way as to be fused to the coding sequence of the bispecific fusion protein. This allows the bispecific fusion protein to be targeted to specific sub-cellular or extra-cellular locations. Various prokaryotic and eukaryotic targeting peptides, and nucleic acid molecules encoding such, are known. In a prokaryotic expression system, a signal sequence can be used to secrete the newly synthesized protein. In an eukaryotic expression system, the targeting peptide would specify targeting of the hybrid protein to one or more specific sub-cellular compartments, or to be secreted from the cell, depending on which peptide is chosen. Through the use of an eukaryotic secretion signal sequence, the bispecific fusion protein can be expressed in a transgenic animal (for instance a cow, pig, or sheep) in such a manner that the protein is secreted into the milk of the animal.

Vectors suitable for stable transformation of culturable cells are also well known. Typically, such vectors include a multiple-cloning site suitable for inserting a cloned nucleic acid molecule, such that it will be under the transcriptional control of 5' and 3' regulatory sequences. In addition, transformation vectors include one or more selectable markers; for bacterial transformation this is often an antibiotic resistance gene. Such transformation vectors typically also contain a promoter regulatory region (e.g., a regulatory region controlling inducible or constitutive expression), a transcription initiation start site, a ribosome binding site, an RNA processing signal, and a transcription termination site, each functionally arranged in relation to the multiple-cloning site. For production of large amounts of recombinant proteins, an inducible promoter can be used. This permits selective production of the recombinant protein, and allows both higher levels of production than constitutive promoters, and enables the production of recombinant proteins that may be toxic to the expressing cell if expressed constitutively.

In addition to these general guidelines, protein expression/purification kits are produced commercially. See, for instance, the QIAEXPRESS™ expression system from QIAGEN (Chatsworth, Calif.) and various expression systems provided by INVITROGEN (Carlsbad, Calif.). Depending on the details provided by the manufactures, such kits can be used for production and purification of the disclosed bispecific fusion proteins.

D. Purification

One skilled in the art will understand that there are myriad ways to purify recombinant polypeptides, and such typical methods of protein purification may be used to purify the disclosed bispecific fusion proteins. Such methods include, for instance, protein chromatographic methods including ion exchange, gel filtration, HPLC, monoclonal antibody affinity chromatography and isolation of insoluble protein inclusion bodies after over production. In addition, purification affinity-tags, for instance a six-histidine sequence, may be recombinantly fused to the protein and used to facilitate polypeptide purification. A specific proteolytic site, for instance a thrombin-specific digestion site, can be engineered into the protein between the tag and the fusion itself to facilitate removal of the tag after purification.

Commercially produced protein expression/purification kits provide tailored protocols for the purification of proteins made using each system. See, for instance, the QIAEXPRESS™ expression system from QIAGEN (Chatsworth, Calif.) and various expression systems provided by INVITROGEN (Carlsbad, Calif.). Where a commercial kit is employed to produce a bispecific fusion protein, the manufacturer's purification protocol is a particularly disclosed protocol for purification of that protein. For instance, proteins expressed with an amino-terminal hexa-his tag can be purified by binding to nickel-nitrilotriacetic acid (Ni-NTA) metal affinity chromatography matrix (*The QIAexpressionist*, QIAGEN, 1997).

Alternately, the binding specificities of either the first or second binding domains, or both, of the disclosed fusion protein may be exploited to facilitate specific purification of the proteins. One method of performing such specific purification would be column chromatography using column resin to which the target molecule, or an epitope or fragment or domain of the target molecule, has been attached.

If the bispecific fusion protein is produced in a secreted form, e.g. secreted into the milk of a transgenic animal, purification will be from the secreted fluid. Alternately, purification may be unnecessary if the fusion protein can be applied directly to the subject in the secreted fluid (e.g. milk).

III. Variation of a Bispecific Fusion Protein

A. Sequence Variants

The binding characteristics and therefore neutralizing activity of the fusion proteins disclosed herein lies not in the precise amino acid sequence, but rather in the three-dimensional structure inherent in the amino acid sequences encoded by the DNA sequences. It is possible to recreate the binding characteristics of any of these proteins or protein domains of this invention by recreating the three-dimensional structure, without necessarily recreating the exact amino acid sequence. This can be achieved by designing a nucleic acid sequence that encodes for the three-dimensional structure, but which differs, for instance by reason of the redundancy of the genetic code. Similarly, the DNA sequence may also be varied, while still producing a functional neutralizing protein.

Variant neutralizing bispecific binding proteins include proteins that differ in amino acid sequence from the disclosed sequence, but that share structurally significant sequence homology with any of the provided proteins. Variation can occur in any single domain of the fusion protein (e.g. the first or second binding domain, or the linker). Variation can also occur in more than one of such domains in any particular variant protein. Such variants may be produced by manipulating the nucleotide sequence of the, for instance a CD4-SCFv(17b)-encoding sequence, using standard procedures, including site-directed mutagenesis or PCR. The simplest modifications involve the substitution of one or more amino acids for amino acids having similar biochemical properties. These so-called conservative substitutions are likely to have minimal impact on the activity of the resultant protein, especially when made outside of the binding site of each domain. Table 1 shows amino acids that may be substituted for an original amino acid in a protein, and which are regarded as conservative substitutions.

TABLE 1

| Original Residue | Conservative Substitutions |
|---|---|
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

More substantial changes in protein structure may be obtained by selecting amino acid substitutions that are less conservative than those listed in Table 1. Such changes include changing residues that differ more significantly in their effect on maintaining polypeptide backbone structure (e.g., sheet or helical conformation) near the substitution, charge or hydrophobicity of the molecule at the target site, or bulk of a specific side chain. The following substitutions are generally expected to produce the greatest changes in protein properties: (a) a hydrophilic residue (e.g., seryl or threonyl) is substituted for (or by) a hydrophobic residue (e.g., leucyl, isoleucyl, phenylalanyl, valyl or alanyl); (b) a cysteine or proline is substituted for (or by) any other residue; (c) a residue having an electropositive side chain (e.g., lysyl, arginyl, or histadyl) is substituted for (or by) an electronegative residue (e.g., glutamyl or aspartyl); or (d) a residue having a bulky side chain (e.g., phenylalanine) is substituted for (or by) one lacking a side chain (e.g., glycine).

Variant binding domain or fusion protein-encoding sequences may be produced by standard DNA mutagenesis techniques, for example, M13 primer mutagenesis. Details of these techniques are provided in Sambrook (*In Molecular Cloning: A Laboratory Manual*, Cold Spring Harbor, N.Y., 1989), Ch. 15. By the use of such techniques, variants may be created which differ in minor ways from the bispecific fusion protein-encoding sequences disclosed. DNA molecules and nucleotide sequences which are derivatives of those specifically disclosed herein and that differ from those disclosed by the deletion, addition, or substitution of nucleotides while still encoding a protein that binds twice to gp120, thereby neutralizing HIV virus infectivity, are comprehended by this invention. In their most simple form, such variants may differ from the disclosed sequences by alteration of the coding region to fit the codon usage bias of the particular organism into which the molecule is to be introduced.

Alternatively, the coding region may be altered by taking advantage of the degeneracy of the genetic code to alter the coding sequence such that, while the nucleotide sequence is substantially altered, it nevertheless encodes a protein having an amino acid sequence substantially similar to the disclosed fusion sequences. For example, the 18th amino acid residue of the CD4-SCFv(17b) protein (after cleavage of the N-terminal signal sequence) is alanine. The nucleotide codon triplet GCT encodes this alanine residue. Because of the degeneracy of the genetic code, three other nucleotide codon triplets—(GCG, GCC and GCA)—also code for alanine. Thus, the nucleotide sequence of the disclosed CD4-SCFv (17b)encoding sequence could be changed at this position to any of these three alternative codons without affecting the amino acid composition or characteristics of the encoded protein. Based upon the degeneracy of the genetic code, variant DNA molecules may be derived from the cDNA and gene sequences disclosed herein using standard DNA mutagenesis techniques as described above, or by synthesis of DNA sequences. Thus, this invention also encompasses nucleic acid sequences which encode a neutralizing bispecific fusion protein, but which vary from the disclosed nucleic acid sequences by virtue of the degeneracy of the genetic code.

B. Peptide Modifications

The present invention includes biologically active molecules that mimic the action of the bispecific fusion proteins of the present invention, and specifically neutralize HIV Env. The proteins of the invention include synthetic embodiments of naturally-occurring proteins described herein, as well as analogues (non-peptide organic molecules), derivatives (chemically functionalized protein molecules obtained starting with the disclosed peptide sequences) and variants (homologs) of these proteins that specifically bind with and neutralize HIV gp120. Each protein of the invention is comprised of a sequence of amino acids, which may be either L- and/or D-amino acids, naturally occurring and otherwise.

Proteins may be modified by a variety of chemical techniques to produce derivatives having essentially the same activity as the unmodified proteins, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the protein, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the protein side chains may be converted to $C_1$-$C_{16}$ alkoxy or to a $C_1$-$C_{16}$ ester using well-recognized techniques. Phenyl and phenolic rings of the protein side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the protein side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the proteins of this invention to select and provide conformational constraints to the structure that result in enhanced stability.

It also may be advantageous to introduce one or more disulfide bonds to connect the frameworks of the heavy and light chains in the SCFv domain. This modification often enhances the stability and affinity of SCFvs (Reiter et al., *Protein Engineering* 7:697-704, 1994). Here too, the X-ray crystal structure containing the 17 FAb (Kwong et al., *Nature* 393:648-659, 1998) can be used to assess optimal sites for engineering cysteine residues of the heavy and light chains.

Peptidomimetic and organomimetic embodiments are also within the scope of the present invention, whereby the three-dimensional arrangement of the chemical constituents of such peptido- and organomimetics mimic the three-dimensional arrangement of the protein backbone and component amino acid side chains in the bispecific neutralizing fusion protein, resulting in such peptido- and organomimetics of the proteins of this invention having measurable or enhanced neutralizing ability. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, *Pharmaceutical Biotechnology*, Interpharm Press: Buffalo Grove, Ill., pp. 165-174 and *Principles of Pharmacology* Munson (ed.) 1995, Ch. 102, for descriptions of techniques used in CADD. Also included within the scope of the invention are mimetics prepared using such techniques that produce neutralizing fusion proteins.

C. Domain Length Variation

It will be appreciated that the protein domains of the current invention may be combined to produce fusion protein molecules without necessarily splicing the components in the same place. It is believed to be possible to use shorter or longer fragments of each component domain, linked by a functional linker. For instance, any component which is spliced within about 10 amino acid residues of the residue specified, and which still provides a functional binding fragment, comprises about the same domain. However, domains of substantially longer or substantially shorter length can be used. For instance, in certain embodiments, the protein can include a leader sequence plus a four-domain CD4 (D1-D4, amino acid residues 1-372), or just the first domain of CD4 (D1 residues 1-113).

IV. Activity of Fusion Proteins

It is important to assess the chemical, physical and biological activity of the disclosed bispecific fusion proteins. Among other uses, such assays permit optimization of the domains chosen, as well as optimization of the length and conformation of the linkers used to connect them. Control molecules should be included in each assay; usually such will include each domain alone, as well as the two domains as separate molecules mixed in the reaction, for instance in a 1:1 molar ratio. In the case of a CD4-SCFv(17b) bispecific fusion protein, such controls would include sCD4 and SCFv(17b), for instance.

A. Fusion Protein Affinity for Target Protein

Fusion protein affinity for the target protein can be determined using various techniques. For instance, co-immunoprecipitation analyses with metabolically labeled proteins can be employed to determine binding of sCD4-SCFv proteins, e.g. sCD4-SCFv(17b) to soluble HIV-1 gp120, using anti-gp120 MAbs that do not interfere with CD4 binding (e.g. MAb D47 that binds to V3), or polyclonal antibody to the C-terminus of gp120. ELISA can also be used to examine the binding characteristics of each domain of the chimera.

B. Neutralization Assays

Various assays can be used to measure the ability of the disclosed fusion proteins to inhibit function of the target protein. Individual components of the fusion protein will serve as controls. In general, assays will be specific for the target/fusion protein. For instance, many functional analyses can test the ability of sCD4-SCFv fusions to neutralize the HIV Env. It is particularly advantageous to use Envs from diverse HIV-1 strains to test the breadth of inhibition (neutralizing ability) of each fusion protein for different HIV-1 genetic subtypes and different phenotypes (i.e. coreceptor usage). In addition, it is advantageous to test such fusion proteins in the standard and sCD4-activated assays for Env-mediated cell fusion. Known HIV-1 neutralizing MAbs and MAbs against CD4-induced epitopes on gp120 are examples of controls for such experiments. Possible synergistic inhibition with other known broadly cross-reactive neutralizing MAbs should be tested (e.g. b12, 2F5, F105, 2G12).

In the case of gp120-targeted fusion proteins, the vaccinia-based reporter gene cell fusion assay may be used to assess fusion inhibition (Nussbaum et al., *J. Virol.* 68:5411-5422, 1994). One population of tissue culture cells (e.g. BS-C-1, HeLa, or NIH 3T3) uniformly expressing vaccinia virus-encoded binding and fusion-mediating viral envelope glycoprotein(s) is mixed with another population expressing the corresponding cellular receptor(s). In the case of sCD4-SCFv fusions, where the target protein is HIV-1 gp120, one cell population expresses HIV-1 Env, while the other expresses necessary HIV-1 receptors (e.g. CD4 and a chemokine receptor). The cytoplasm of either cell population also contains vaccinia virus-encoded bacteriophage T7 DNA polymerase; the cytoplasm of the other contains a transfected plasmid with the *E. coli* lacZ gene linked to the T7 promoter. Upon mixing of the two populations, cell fusion results in activation of the lacZ gene, through the introduction of the T7 RNA polymerase into proximity with the transfected T7 promoter-lacZ in the cytoplasm of the fused cells. The resultant β-galactosidase (β-gal) activity is proportional to the amount of fusion that occurs, and can be measured by colorimetric assay of detergent cell lysates or in situ staining. Cell-fusion neutralizing activity of bispecific fusion proteins is therefore assessed by measuring their inhibition of β-gal production.

The gp120-targeted fusions (e.g. sCD4-SCFv) can also be tested for ability to block HIV-1 infection using single round assays (e.g. using indicator cell lines, Vodicka et al., *Virology* 233:193-198, 1997). Target cells expressing CD4 and a specific coreceptor, and containing the lacZ reporter gene linked to the HIV-1 long terminal repeat (LTR), are infected with specific HIV-1 strains (Vodicka, 1997). Integration of an HIV provirus in these cells leads to production of the viral trans-activator, Tat, which then turns on expression of the β-gal gene via interaction with LTR. The activity of sCD4-SCFv is assessed by its inhibition of production of β-gal-positive cells (stained blue with X-gal), which is proportional to its ability to block HIV-1 infection.

V. Incorporation of Bispecific Fusion Proteins into Pharmaceutical Compositions Pharmaceutical compositions that comprise at least one bispecific fusion protein as described herein as an active ingredient will normally be formulated with a solid or liquid carrier, depending upon the particular mode of administration chosen. The pharmaceutically acceptable carriers and excipients useful in this invention are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, other proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate.

Other medicinal and pharmaceutical agents, for instance nucleoside derivatives (e.g. AZT) or protease inhibitors, also may be included. It may also be advantageous to include other fusion inhibitors, for instance one or more neutralizing antibodies.

The dosage form of the pharmaceutical composition will be determined by the mode of administration chosen. For instance, in addition to injectable fluids, topical and oral formulations can be employed. Topical preparations can include eye drops, ointments, sprays and the like. Oral formulations may be liquid (e.g., syrups, solutions or suspensions), or solid (e.g., powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those skilled in the art.

The pharmaceutical compositions that comprise bispecific fusion protein may be formulated in unit dosage form, suitable for individual administration of precise dosages. One possible unit dosage contains approximately 100 µg of protein. The amount of active compound administered will be dependent on the subject being treated, the severity of the affliction, and the manner of administration, and is best left to the judgment of the prescribing clinician. Within these bounds, the formulation to be administered will contain a quantity of the active component(s) in an amount effective to achieve the desired effect in the subject being treated.

VI. Clinical Use of Bispecific Fusion Proteins

The potent viral-neutralizing activity exhibited by the disclosed bispecific fusion proteins makes them useful for treating viral infections in human and other animal subjects. Possibly susceptible viruses include the immunodeficiency viruses, such as HIV and similar or related viruses in simians and other animals. In addition, other viral or microbial systems that involve the interaction of a first inducing and second induced binding site of a single protein will also be susceptible to neutralization using bispecific fusion proteins of the current invention. The bispecific fusion proteins disclosed herein can also be used in highly sensitive detection or purification of target protein.

The bispecific fusion proteins of this invention may be administered to humans, or other animals on whose cells they are effective, in various manners such as topically, orally, intravenously, intramuscularly, intraperitoneally, intranasally, intradermally, intrathecally, and subcutaneously. The particular mode of administration and the dosage regimen will be selected by the attending clinician, taking into account the particulars of the case (e.g., the subject, the disease, and the disease state involved, and whether the treatment is prophylactic or post-infection). Treatment may involve daily or multi-daily doses of bispecific fusion protein(s) over a period of a few days to months, or even years.

If treatment is through the direct administration of cells expressing the bispecific fusion protein to the subject, such cells (e.g. transgenic pluripotent or hematopoietic stem cells or B cells) may be administered at a dose of between about $10^6$ and $10^{10}$ cells, on one or several occasions. The number of cells will depend on the patient, as well as the fusion protein and cells chosen to express the protein.

A general strategy for transferring genes into donor cells is disclosed in U.S. Pat. No. 5,529,774, which is incorporated by reference. Generally, a gene encoding a protein having therapeutically desired effects is cloned into a viral expression vector, and that vector is then introduced into the target organism. The virus infects the cells, and produces the protein sequence in vivo, where it has its desired therapeutic effect. See, for example, Zabner et al., *Cell* 75:207-216, 1993. As an alternative to adding the sequences encoding the bispecific fusion protein or a homologous protein to the DNA of a virus, it is also possible to introduce such a gene into the somatic DNA of infected or uninfected cells, by methods that are well known in the art (Sambrook et al., In *Molecular Cloning: A Laboratory Manual*, Cold Spring Harbor, N.Y., 1989). These methods can be used to introduce the herein disclosed fusion proteins to human cells to provide long-term resistance to HIV-1 infection or AIDS. For example, gene therapy can be used to secrete the protein at mucosal surfaces, such as the vaginal, rectal, or oral mucosa.

HIV-1 gp120-targeted bispecific fusion proteins, for instance sCD4-SCFv(17b), are particularly useful in the prevention of infection during or immediately after HIV exposure (e.g., mother/infant transmission, post-exposure prophylaxis, and as a topical inhibitor). In such instances, one or more doses of the bispecific fusion protein are administered before or soon after the triggering event. To prevent or ameliorate mother/infant transmission of viral infection, for instance, it may be beneficial to administer the gp120-targeted bispecific fusion protein to the mother intermittently throughout pregnancy, and/or immediately before or following delivery, and/or directly to the newborn immediately after birth. Post-exposure prophylactic treatments may be particularly beneficial where there has been accidental exposure (for instance, a medically related accidental exposure), including but not limited to a contaminated needle-stick or medical exposure to HIV-1 contaminated blood or other fluid.

The present invention also includes combinations of chimeric bispecific fusion proteins with one or more other agents useful in the treatment of disease, e.g. HIV disease. For example, the compounds of this invention may be administered, whether before or after exposure to the virus, in combination with effective doses of other anti-virals, immuno-modulators, anti-infectives, and/or vaccines. The term "administration in combination" refers to both concurrent and sequential administration of the active agents.

Examples of antiviral agents that can be used in combination with the chimeric bispecific fusion proteins of the invention are: AL-721 (from Ethigen of Los Angeles, Calif.), recombinant human interferon beta (from Triton Biosciences of Alameda, Calif.), Acemannan (from Carrington Labs of Irving, Tex.), gangiclovir (from Syntex of Palo alto, Calif.), didehydrodeoxythymidine or d4T (from Bristol-Myers-Squibb), EL10 (from Elan Corp. of Gainesville, Ga.), dideoxycytidine or ddC (from Hoffman-LaRoche), Novapren (from Novaferon labs, Inc. of Akron, Ohio), zidovudine or AZT (from Burroughs Wellcome), ribaririn (from Viratek of Costa Mesa, Calif.), alpha interferon and acyclovir (from Burroughs Wellcome), Indinavir (from Merck & Co.), 3TC (from Glaxo Wellcome), Ritonavir (from Abbott), Saquinavir (from Hoffmann-LaRoche), and others.

Examples of immuno-modulators that can be used in combination with the chimeric bispecific fusion proteins of the invention are AS-101 (Wyeth-Ayerst Labs.), bropirimine (Upjohn), gamma interferon (Genentech), GM-CSF (Genetics Institute), IL-2 (Cetus or Hoffman-LaRoche), human immune globulin (Cutter Biological), IMREG (from Imreg of New Orleans, La.), SK&F106528, and TNF (Genentech).

Examples of some anti-infectives with which the chimeric bispecific fusion proteins can be used include clindamycin with primaquine (from Upjohn, for the treatment of *Pneumocystis pneumonia*), fluconazlone (from Pfizer for the treatment of cryptococcal meningitis or candidiasis), nystatin, pentamidine, trimethaprim-sulfamethoxazole, and many others.

The combination therapies are of course not limited to the lists provided in these examples, but includes any composition for the treatment of HIV disease (including treatment of AIDS).

VII. Kits

The chimeric proteins disclosed herein can be supplied in the form of a kit for use in prevention and/or treatment of diseases (e.g., HIV infection and AIDS). In such a kit, a clinically effective amount of one or more of the chimeric bispecific fusion proteins is provided in one or more containers. The chimeric bispecific fusion proteins may be provided suspended in an aqueous solution or as a freeze-dried or lyophilized powder, for instance. In certain embodiments, the chimeric proteins will be provided in the form of a pharmaceutical composition.

Kits according to this invention can also include instructions, usually written instructions, to assist the user in treating a disease (e.g., HIV infection or AIDS) with a chimeric bispecific fusion protein. Such instructions can optionally be provided on a computer readable medium.

The container(s) in which the protein(s) are supplied can be any conventional container that is capable of holding the supplied form, for instance, microfuge tubes, ampoules, or bottles. In some applications, chimeric proteins may be provided in pre-measured single use amounts in individual, typically disposable, tubes or equivalent containers.

The amount of a chimeric bispecific fusion protein supplied in the kit can be any appropriate amount, depending for instance on the market to which the product is directed. For instance, if the kit is adapted for research or clinical use, the amount of each chimeric protein provided would likely be an amount sufficient for several treatments.

Certain kits according to this invention will also include one or more other agents useful in the treatment of disease, e.g. HIV disease. For example, such kits may include one or more effective doses of other anti-virals, immunomodulators, anti-infectives, and/or vaccines.

Example 1

Construction of a CD4-SCFv(17b) Encoding Sequence

Figure 3:
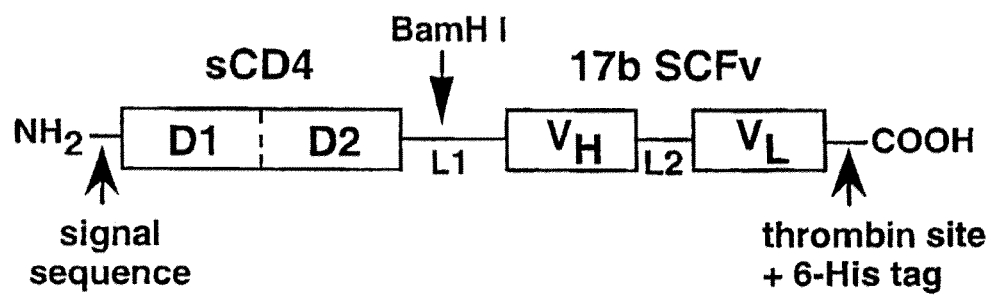
FIG. 3 is a schematic diagram of the CD4-SCFv(17b) genetic construct. The genetic construct encodes sCD4 (D1D2, plus the native CD4 N-terminal signal sequence), followed by the L1 linker (Gly$_4$Ser)$_7$, which attaches the 17b SCFv (V$_H$ attached to V$_L$ via the L2 linker (Gly$_4$Ser)$_3$), followed by the thrombin cleavage site and hexa-his tag. There is a BamH I site in the middle of L1 to facilitate production of constructs of different lengths.
Figure 4:
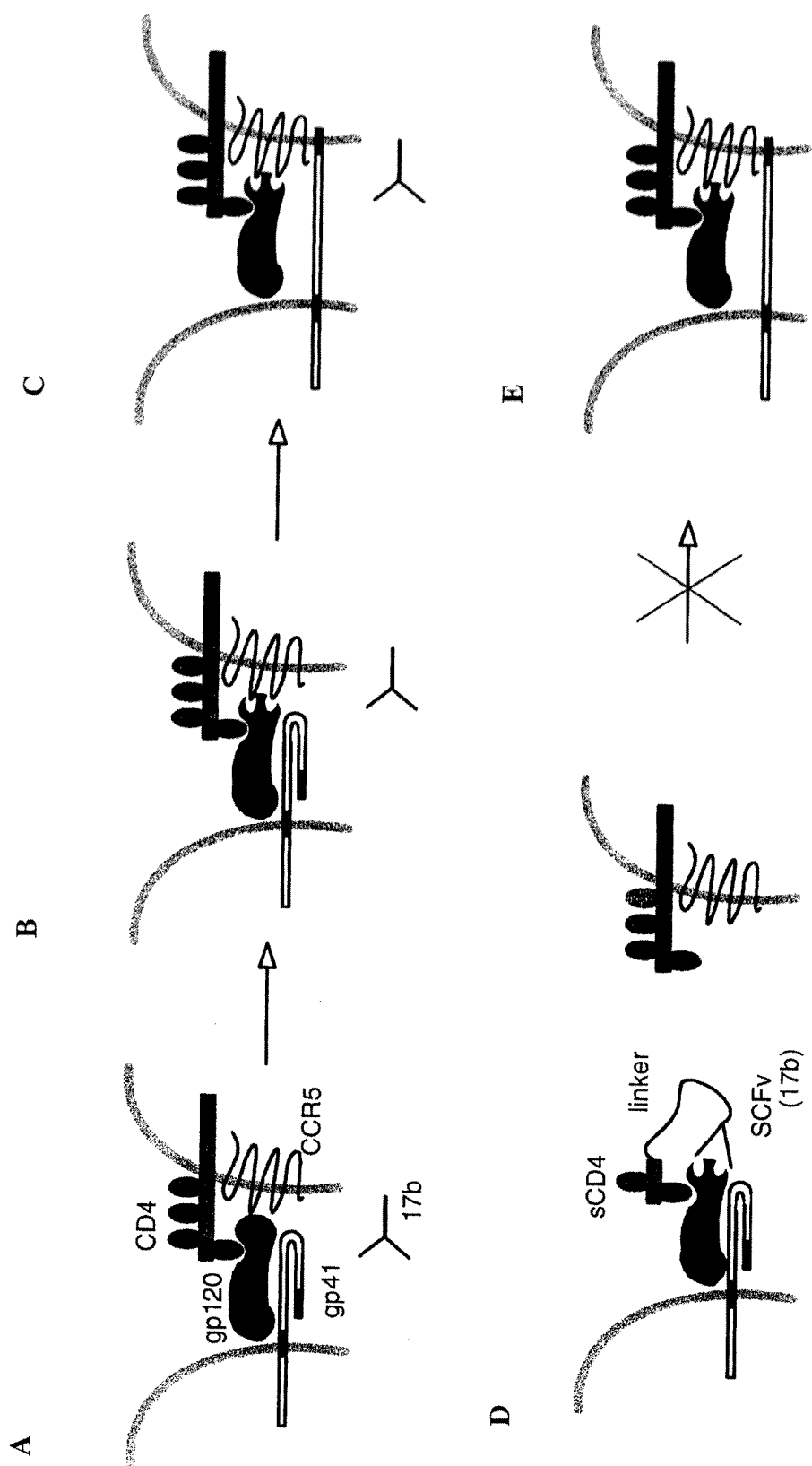
FIG. 4 is a drawing of mechanisms of binding of a sCD4-SCFv(17b) to gp120, and the resulting neutralization of HIV Env function (fusion and infectivity).

A gp120-targeted fusion protein, sCD4-SCFv(17b), is constructed by linking the C-terminus of CD4 (D1D2, 183 amino acid residues) to the N-terminus of the heavy chain of the 17b SCFv, which contains the heavy chain at its N-terminus, linked via its C-terminus to the N-terminus of the light chain (see schematic diagram of the construct, FIG. 3). The 17b SCFv DNA was obtained from R. Wyatt and J. Sodroski, Dana Farber Cancer Institute, Boston, Mass. The 17b-MAb producing-hybridoma was obtained from J. Robinson, Tulane University.

Linkers were chosen to have sufficient length and flexibility to connect the desired protein segments without inducing unacceptable torsion. For the SCFv, the 15 amino acid residue sequence $(Gly_4Ser)_3$ (designated L2) was chosen, which has been employed successfully for production of SCFvs. This sequence confers excellent flexibility with minimal aggregation. The linker between the C-terminus of CD4 and the N-terminus of the SCFv (designated L1; SEQ ID NO: 2), is seven repeats of the same $Gly_4Ser$ sequence. Conservative estimates indicate that this 35 amino acid residue linker is sufficiently long to allow CD4 and SCFv to bind simultaneously to their respective binding sites on gp120. A schematic of the genetic construct is shown in FIG. 3. A unique BamH I restriction site has been introduced within L1 to enable the production of constructs with shorter or longer linkers, and especially to provide negative controls (linkers too short, thereby not allowing both the CD4 and SCFv moieties of a single molecule to bind simultaneously to their respective binding sites on gp120).

The starting CD4 plasmid is pCB-3, which contains the full-length CD4 cDNA (including its natural 5' signal sequence) in the vaccinia expression plasmid pSC59 (Broder & Berger, *J. Virol.* 67:913-926, 1993). This plasmid was digested with Stu I, which cuts near the end of the 2nd domain of sCD4, and with Spe I, which cuts within the vector downstream of the CD4 insert and leaves a 5' overhang.

Synthetic oligonucleotides (SEQ ID NO: 11) were annealed together to recapitulate the 5' end of the second half of the Stu I site (CCT) and the next two bases (CC) of the CD4 cDNA, and to produce an Spe I overhang at the 3' end (this site to be destroyed upon ligation into pCB-3). The oligonucleotide sequence reconstructs the remainder of the second domain of CD4 (through $ser_{183}$), and encodes the 37 amino acid intermediate linker $(gly_4ser)_6gly_4thr_2ser$, followed directly by the universal translational termination sequence (UTS) (SEQ ID NO: 6). A BamH I site has been deliberately included within the linker near the end of the third $(gly_4ser)$ repeat, to enable subsequent linkage to the 17b SCFv with the exact L1 sequence, and to enable modification of linker length. The resulting intermediate plasmid is designated pCD1. This construct was confirmed by DNA sequence analysis using standard techniques. To facilitate subsequent procedures, the sCD4-linker sequence was recloned into a pSC59 derivative lacking a BamH I site, forming intermediate plasmid pCD2.

The starting 17b plasmid containing the 17b SCFv cDNA in a plasmid vector (pmt del 0) was donated by Dr. Richard Wyatt (Dana Farber Cancer Institute, Boston, Mass.). The SCFv cDNA is constructed with the heavy chain at the 5' segment and light chain at the 3' segment, attached via DNA encoding the L2 linker $(gly_4ser)_3$. The 17b SCFv construct has a TPA signal sequence at the 5' end, and sequences corresponding to a thrombin cleavage site and a hexa-his tag (to facilitate purification) at the 3' end, followed by a stop codon. A comparable construct without the thrombin cleavage site and hexa-his tag can also be produced.

PCR technology was used to attach the 17b SCFv sequence to the CD4-linker sequence in pCD2. Suitable primers are represented in SEQ ID NOs: 7 and 9. The forward (5') primer (SEQ ID NO: 7) contains a BamH I site near the 5' end (preceded by an overhang), followed by nucleotides that reconstruct the third $(gly_4ser)$ plus four additional $(gly_4ser)$ repeats; this is followed by nucleotides exactly corresponding to the start of the 17b heavy chain (excluding the 5' signal sequence, beginning at CAG GTG). The 3' primer (SEQ ID NO: 9) begins with convenient restriction sites for cloning into pCD2 (Spe I and others), followed by nucleotides exactly complementary to the 3' end of the 17b SCFv sequence in pmt del 0 (stop codon, hexa-his tag, and thrombin cleavage site).

These primers are used to prime the plasmid vector containing the 17b SCFv sequence in pmt del 0, and the resultant PCR product digested with BamH I plus a restriction enzyme that cleaves at the opposite 3' end (e.g., Spe I). This digested fragment is then force-cloned into pCD2 that has been digested with the same enzymes (BamH I and Spe I). The resulting plasmid (designated herein as pCD3) contains the final sCD4-SCFv(17b) construct (with the thrombin cleavage site and hexa-his tag) downstream from the strong, synthetic early/late vaccinia promoter in pSC59. There are convenient, unique restriction sites on each side of the sCD4-SCFv sequence for possible future cloning steps.

The 17b SCFv cDNA (including the 5' signal sequence) also has been excised from the pmt del 0 vector by restriction enzyme digestion or PCR, and cloned into the vaccinia expression plasmid pSC59 to provide a control construct.

Example 2

Expression and Purification of CD4-SCFv(17b) Fusion Protein

A. Expression

For small amounts of protein expression, vaccinia expression technology can be used to produce the sCD4-SCFv(17b) (as well as the control 17b SCFv protein). The plasmid containing the construct in the vaccinia expression plasmid pSC59 is used to produce a vaccinia recombinant, using standard technology. For such expression, suitable cells (HeLa, BSC-1, etc.) are infected with the recombinant vaccinia virus; after incubation for 24-36 hours at 37° C., the recombinant protein is present in the culture supernatant. Initial biochemical and functional studies can be done with unfractionated supernatant; where necessary, the sCD4-SCFv protein may be purified (see below). Small scale, initial experiments can be performed with small amounts of material (5-20 micrograms, obtained from $1-5 \times 10^7$ cells). The preparation can be scaled up; for such large-scale production, it may be advantageous to employ higher yield technologies for expression of the recombinant proteins (e.g., baculovirus, yeast, or *E. coli*).

Expression of the pCD1 secreted protein product (the first two domains of CD4 through $ser_{183}$, plus the 37 amino acid linker) was analyzed. BSC-1 cells were transfected with pCD1 and infected with wild type vaccinia virus, then incubated overnight at 37° C. Supernatants were analyzed by Western (immnunoblot) analysis, using antibodies against CD4. As expected, the protein encoded by pCD1 migrated slightly more slowly than standard purified two-domain sCD4 (Upjohn-Pharmacia, Kalamazoo, Mich.).

The pCD3 full-length sCD4-SCFv(17b) (sCD4-17b) fusion protein has been expressed and tested similarly, and 17b SCFv domain (as cloned into pSC59) can be examined likewise. The sCD4-17b fusion protein (at least a portion of which is secreted) has the expected molecular size (approximately 55 kD) when analyzed by SDS PAGE and Western blotting. The protein reacted strongly with antibodies against CD4 or the hexa-his tag, confirming the presence of these N-terminal and C-terminal moieties, as well as the correct reading frame.

B. Purification

Expressed fusion protein as constructed above with an amino-terminal hexa-his tag was purified using this molecular tag. The tag enables the specific binding and purification of the fusion protein by binding to nickel-nitrilotriacetic acid (Ni-NTA) metal affinity chromatography matrix (see, for instance, *The QIAexpressionist*, QIAGEN, 1997). A hexa-his tag was used in the present examples.

Alternative purification methods include a combination of HPLC and conventional liquid column chromatography (gel filtration; ion exchanger; isoelectric focusing).

C. Primary Characterization

In order to test gp120 binding to the 17b domain of the sCD4-17b fusion protein, 96-well ELISA plates were first coated with the 13B8.2 anti-CD4 MAb (Beckman Coulter, Chaska, Minn., Catalogue no. IM0398), whose epitope on CD4 overlaps determinants involved in binding to gp120. The plates were then incubated with either the purified sCD4-17b or control buffer. When the chimeric protein was captured this way, the 17b moiety remained available to bind gp120 complexed to sCD4; however the sCD4 moiety could not bind free gp120, since it was captured on the plate by the anti-CD4 MAb that blocks the binding site. The plates were incubated with gp120 (IIIB isolate, Ratner et al., *Nature* 313:277-284, 1985) complexed to sCD4. Binding of gp120 was detected by a polyclonal anti-gp120 antiserum, followed by anti-rabbit IgG conjugated to horseradish peroxidase. The plates were washed and incubated with ABTS substrate, and the oxidized product was quantitated by measuring absorbance at 405 nm. The results indicated specific binding: absorbance values were 0.15 with the sCD4-17b chimeric protein, compared to 0.05 with the control buffer.

For testing functionality of the sCD4 region of the chimeric protein, the ELISA plates were first coated with an anti-His tag MAb (QIAGEN Inc., Valencia, Calif., Catalog no. 34670), then incubated with either the purified chimeric protein or control buffer. With the chimeric protein captured in this way, the sCD4 moiety was available to bind free gp120; however the 17b moiety could not bind gp120 that was not complexed to sCD4. The plates were incubated with free gp120, and binding was detected as detailed above. The results indicated specific binding: absorbance values were 0.46 with sCD4-17b, compared to 0.05 with the control buffer. Thus, the ELISA assays confirmed the expected functional binding properties for each moiety of the chimeric protein: 17b moiety bound the gp120/sCD4 complex, and the CD4 moiety bound free gp120.

Example 3

HIV-Envelope Neutralization Measurements

A. Vaccinia-Based Reporter Gene Cell Fusion

Env-mediated cell fusion activated by CD4 was measured using the vaccinia-based reporter gene assay (Nussbaum et al., *J. Virol.* 68:5411-5422, 1994). For the experiment shown in Table 2 and FIG. 1, effector cells (HeLa) were transfected with plasmid pG1NT7-β-gal (lacZ linked to T7 promoter), then infected with vaccinia recombinants encoding either the mutant uncleaved Unc Env or the wildtype (WT) SF162 Env (Broder & Berger, *Proc. Natl. Acad. Sci., USA* 92:9004-9008, 1995). Target cells were created by transfecting NIH 3T3 cells with plasmid pGA9-CKR5, containing the CCR5 cDNA linked to a vaccinia promoter (Alkhatib et al., *Science* 272: 1955-1958, 1996), then infecting these cells with wild type vaccinia virus WR. Target cells also carry and express a bacteriophage T7 RNA polymerase. Prior to fusion assays, transfected cells were incubated overnight at 31° C. to allow expression of recombinant proteins, then washed.

For each fusion assay, mixtures of effector and target cells ($1\times10^5$ of each cell type per well, duplicate wells) were prepared in the absence or presence of sCD4 (100 nM final). After 2.5 hours at 37° C., cells were lysed with NP-40 and β-gal activity was quantitated using standard procedures (Table 2 and FIG. 1). Relative fusion (specific β-gal activity) was determined from the mean of duplicate samples, and calculated as WT-Unc.

TABLE 2

Vaccinia-based reporter gene cell fusion assay using soluble CD4

| | Total β-gal (Raw data) | | | | | | |
|---|---|---|---|---|---|---|---|
| | Unc Env (Control) | | | WT Env (SF162) | | | Relative fusion (WT − Unc) |
| | duplicates | | mean | duplicates | | mean | |
| −sCD4 | 0.50 | 0.40 | 0.45 | 0.50 | 0.40 | 0.45 | 0.0 |
| +sCD4 | 0.40 | 0.50 | 0.45 | 6.60 | 5.20 | 5.90 | 5.45 |

This vaccinia-based fusion assay can be used to assess the neutralizing ability of the herein disclosed bispecific fusion proteins. The neutralizing ability of MAb 17b was demonstrated to be dependent on the addition of soluble CD4 as follows (see Table 3 and FIG. 2). Effector cells were created by co-infecting HeLa cells with a vaccinia recombinant encoding HIV-1 Env (LAV) (Broder & Berger, *Proc. Natl. Acad. Sci., USA* 92:9004-9008, 1995), and another encoding T7 RNA polymerase. Target cells were created by co-transfecting NIH 3T3 cells with plasmids pYF1-fusin (Feng et al., *Science* 272:872-877, 1996) encoding CXCR4, and pGlNT7-β-gal (lacZ linked to the T7 promoter). The target cells were then infected with vaccinia viruses vCB-3 (encoding CD4, standard assay) (Broder et al., *Virology* 193:483-491, 1993), or WR (wild type virus, sCD4 assay). As background controls, target cells were transfected with pG1NT7-β-gal only (i.e., no coreceptor). Transfected cells were incubated overnight at 31° C. to allow expression of recombinant proteins, then washed. Effector cells were incubated 30 minutes at 37° C. with the indicated concentration of MAb 17b (Table 3).

For fusion assays, mixtures were prepared between effector and indicated target cells ($2\times10^5$ of each cell type per well, duplicate wells); in the standard assay, target cells expressed CXCR4 and CD4, and no soluble CD4 added; in the sCD4 assay, target cells expressed CXCR4 alone, and soluble CD4 was added (200 nM final). After 2.5 hours at 37° C., cells were lysed and β-gal activity was quantitated. Background control β-gal values (standard assay, 0.6; sCD4 assay, 0.2), obtained with target cells lacking coreceptor, were subtracted to give the data presented in Table 3. Data represent percentage of control (no MAb) for each assay.

TABLE 3

MAb-mediated inhibition of fusion assay

| [17b] | Standard Assay | | sCD4 Assay | |
|---|---|---|---|---|
| (μg/ml) | β-gal | % control | β-gal | % control |
| none | 42.3 | 100.0 | 11.89 | 100.0 |
| 0.1 | 39.5 | 93.4 | 13.55 | 113.9 |
| 0.5 | 43.9 | 103.8 | 4.66 | 39.2 |
| 1 | 39.8 | 94.1 | 1.68 | 14.1 |
| 5 | 50.5 | 119.4 | 0 | 0 |

The effectiveness of the herein described bispecific fusion proteins for neutralizing fusion is tested in a similar manner, by adding varying amounts of the bispecific fusion protein, e.g. sCD4-SCFv(17b), to the above assay. Exogenous sCD4 and SCFv(17b) or other gp120-binding proteins need not be added, though they can be used as controls as above, or to determine relative inhibitory efficiencies compared to the bispecific fusion protein. Using this assay, the effects of media from control cells infected with wild-type vaccinia virus WR, were compared with media from cells infected with the recombinant vaccinia virus encoding sCD4-17b. The relative specific β-galactosidase values were 23.4 with the control media and <1 with sCD4-SCFv media. Thus, the chimeric sCD4-17b protein strongly inhibited HIV-1 Env-mediated cell fusion.

Example 4

Large Scale Production and Analysis of sCD4-17b

To produce large amounts of the sCD4-17b protein, the DNA construct has been transferred to the pET11b plasmid vector (Novagen, Madison, Wis., Catalog no. 69437-3), which is suitable for high level inducible expression in *E. coli*. This system involves cloning of target genes under control of strong bacteriophage T7 transcription signal. Once established in a non-expression host bacterial cell, plasmids are then transferred into expression hosts containing a chromosomal copy of the T7 RNA polymerase gene under lacUV5 control, and expression of the recombinant protein of interest (here, sCD4-17b) is induced by the addition of IPTG. The expressed protein is produced at a very high level, and may constitute more than 50% of the total cell protein in the induced culture within a few hours after induction. Western blot results indicate high level expression of the sCD4-17b from the pET11b plasmid.

The protein produced can be denatured and renatured from inclusion bodies to provide a large quantity of functional sCD4-17b protein. This protein can be used for in vitro studies to test inhibition in assays of both Env-mediated cell fusion and HIV infection (p24 production).

In addition, the sCD4-17b protein can be used for in vivo studies. One in vivo model involves SCID mice reconstituted with human thymus plus liver (Pettoello-Montovani et al., *J. Infect. Dis.* 177:337-346, 1998); this system will be used to test whether sCD4-17b inhibits (and to what extent), or prevents, acute HIV-1 infection. This system has been successfully used to demonstrate potent blocking activities of other anti-HIV agents (e.g., protease inhibitors and reverse transcriptase inhibitors, and Env-targeted toxins) (Pettoello-Montovani et al., *J. Infect. Dis.* 177:337-346, 1998).

A second example of an in vivo system for testing sCD4-17b activity involves rhesus macaques challenged with SHIV viruses (recombinant viruses containing SIV gag and pol, plus an HIV envelope; Li et al., *J. Virol.* 69:7061-7071, 1995). This system will be used to test whether the sCD4-17b protein inhibits (and to what extent), or prevents, acute SHIV infection.

The effects of sCD4-17b against chronic infection will also be examined, again using the SCID-hu/HIV-1 mouse system and the macaque/SHIV system.

Both in vitro and in vivo study systems also will be used to test the potency of sCD4-17b protein when used in combination with other anti-HIV agents (e.g., RT and protease inhibitors or other HIV-1 neutralizing MAbs).

The foregoing examples are provided by way of illustration only. Numerous variations on the biological molecules and methods described above may be employed to make and use bispecific fusion molecules capable of binding to two sites on a single protein, and especially two sites on the HIV envelope protein gp120, and for their use in detection, treatment, and prevention of HIV infection. We claim all such subject matter that falls within the scope and spirit of the following claims.

We claim:

1. A neutralizing bispecific fusion protein capable of binding to two sites on gp120, comprising a first binding domain capable of binding to an inducing site on gp120, thereby exposing an induced epitope; a second binding domain capable of forming a neutralizing complex with an induced epitope of gp120; and a linker connecting the first domain to the second domain wherein the first binding domain comprises CD4 D1 or CD4 D1D2 and the second domain comprises SCFv48d or SCFvCG10, and wherein the linker maintains the second binding domain in binding proximity to the induced epitope when the first binding domain is bound to the inducing site.

2. The protein according to claim 1, wherein the linker is substantially flexible.

3. The protein according to claim 1, wherein the linker is 15-100 angstroms (Å) long.

4. The protein according to claim 1, wherein the linker is 10-100 amino acid residues in length.

5. A protein according to claim 1, wherein the linker comprises at least one occurrence of an amino acid sequence represented by SEQ ID NO: 1.

6. A protein according to claim 5, wherein the linker comprises an amino acid sequence represented by SEQ ID NO: 2.

7. A composition comprising the protein according to claim 1.

8. A composition comprising the protein according to claim 1 and a pharmaceutically acceptable carrier.

9. A kit, comprising the neutralizing bispecific fusion protein of claim 1.

10. The kit of claim 9, further comprising instructions.

11. The kit of claim 10, wherein the instructions include directions for administering at least one dose of the neutralizing bispecific fusion protein to a subject in need of treatment and/or prevention of HIV infection.

12. The kit of claim 9, wherein the neutralizing bispecific fusion protein is provided in the form of a composition.

* * * * *